United States Patent [19]

Donovan et al.

[11] Patent Number: 5,264,364
[45] Date of Patent: Nov. 23, 1993

[54] BACILLUS THURINGIENSIS CRYIIIC(B) TOXIN GENE AND PROTEIN TOXIC TO COLEOPTERAN INSECTS

[75] Inventors: Willam P. Donovan, Levittown, Pa.; Mark J. Rupar, Wilmington, Del.; Annette C. Slaney, Hamilton Square, N.J.

[73] Assignee: Ecogen Inc., Langhorne, Pa.

[21] Appl. No.: 32,775

[22] Filed: Mar. 15, 1993

Related U.S. Application Data

[63] Continuation of Ser. No. 813,592, Dec. 23, 1991, abandoned, continuation-in-part of Ser. No. 649,562, Jan. 31, 1991, abandoned.

[51] Int. Cl.$^5$ .................. C12N 1/20; A01N 63/00; C12Q 1/68; C12P 21/06
[52] U.S. Cl. .................. 435/252.5; 424/93 L; 435/6; 435/69.1; 435/252.3; 435/320.1; 536/22.1; 536/23.1; 536/23.2; 536/23.7; 536/23.71
[58] Field of Search ............... 424/93 L; 435/6, 69.1, 435/252.3, 252.5, 320.1; 536/22.1, 23.1, 23.2, 23.7, 23.71

[56] References Cited

U.S. PATENT DOCUMENTS

| | | | |
|---|---|---|---|
| 4,766,203 | 8/1988 | Krieg et al. | 530/370 |
| 4,771,131 | 9/1988 | Herrnstadt et al. | 536/27 |
| 4,797,279 | 1/1989 | Karamata et al. | 424/93 |
| 4,910,016 | 3/1990 | Gaertner et al. | 424/93 |
| 4,966,765 | 10/1990 | Payne et al. | 424/93 |
| 4,996,155 | 2/1991 | Sick et al. | 435/252.3 |
| 4,999,192 | 3/1991 | Payne et al. | 424/93 |
| 5,006,336 | 4/1991 | Payne | 424/93 |
| 5,024,837 | 6/1991 | Donovan et al. | 424/93 |
| 5,055,293 | 10/1991 | Aronson et al. | 424/93 |
| 5,187,091 | 2/1993 | Donovan et al. | 435/240.4 |

FOREIGN PATENT DOCUMENTS

| | | |
|---|---|---|
| 289479 | 11/1988 | European Pat. Off. |
| 318143 | 5/1989 | European Pat. Off. |
| 324254 | 7/1989 | European Pat. Off. |
| 328383 | 8/1989 | European Pat. Off. |
| 337604 | 10/1989 | European Pat. Off. |
| 346114 | 12/1989 | European Pat. Off. |
| 382990 | 8/1990 | European Pat. Off. |
| 9013651 | 11/1990 | PCT Int'l Appl. |
| 9107481 | 5/1991 | PCT Int'l Appl. |
| 91-16433 | 10/1991 | PCT Int'l Appl. |
| 9114778 | 10/1991 | PCT Int'l Appl. |

OTHER PUBLICATIONS

Cidaria et al., *FEMS Microbiol. Lett.* 81 (1991) 129-134, "A novel strain of Bacillus-thuringiensis (NCIMB 40152) active against coleopteran insects."

Lambert et al., First Intl. Conf. on Mol. Biol. of *Bacillus thuringiensis* San Francisco, Jul. 26-28, 1991, Abstract: "CryIIIC, a novel crystal protein gene from *Bacillus thuringiensis* subsp. *galleriae* isolate".

Sick et al., *Nucleic Acids Res.* 18, p. 1305 (1990) "Nucleotide sequence of a coleopteran-active toxin gene from a new isolate of *Bacillus thuringiensis* subsp. *tolworthi*".

Höfte et al., *Microbial. Rev.* 53, pp. 242-255 (1989) "Insecticidal Crystal Proteins of *Bacillus thuringiensis*".

Donovan et al., *Mol. Gen. Genet.*, 214, pp. 365-372 (1988) "Isolation and characterization of EG 2158, a new strain of *Bacillus thuringiensis* toxic to coleopteran larvae, and nucleotide sequence of the toxin gene".

(List continued on next page.)

Primary Examiner—Robert A. Wax
Assistant Examiner—Hyosuk Kim
Attorney, Agent, or Firm—Christopher Egolf; Alan S. Nadel

[57] ABSTRACT

A *Bacillus thuringiensis* strain isolate, designated EG5144, exhibits insecticidal activity against coleopteran insects, including Colorado potato beetle and insects of the genus Diabrotica. A novel toxin gene in B.t. strain EG5144 produces an irregularly shaped insecticidal crystal protein of approximately 70 kDa that is toxic to coleopteran insects. The cryIII-type gene (SEQ ID NO:1), designated as the cryIIIC(b) gene, has a nucleotide base sequence illustrated in FIG. 1.

9 Claims, 8 Drawing Sheets

OTHER PUBLICATIONS

McPherson et al., *Bio/Technology*, 6, pp. 61–66 (1988) "Characterization of the Coleopteran-Specific Protein Gene of *Bacillus thuringiensis* var. *tenebrionis*".

Sekar et al., *Proc. Natl. Acad. Sci. USA*, 84, pp. 7036–7040 (1987) "Molecular cloning and characterization of the insecticidal crystal protein gene of *Bacillus thuringiensis* var. *tenebrionis*".

Höfte et al., *Nucleic Acids Research*, 15, pp. 7183 (1987) "Nucleotide sequence of a gene encoding an insecticidal protein of *Bacillus thuringiensis* var. *tenebrionis* toxic against Coleoptera".

Herrnstadt et al., *Gene*, 57, pp. 37–46 (1987) "Nucleotide sequence and deduced amino acid sequence of a coleopteran-active delta-endotoxin gene from *Bacillus thuringiensis* subsp. *san diego*".

Krieg et al., *J. Appl. Ent.*, 104, pp. 417–424 (1987) "*Bacillus thuringiensis* subsp. *tenebrionis* Stamm BI 256–82".

Herrnstadt et al., *Bio/Technology*, 4, pp. 305–308 (1986) "A new strain of *Bacillus thuringiensis* with activity against coleopteran insects".

Bernhard, *FEMS Microbiol. Lett.*, 33, pp. 261–265 (1986) "studies on the delta-endotoxin of *Bacillus thuringiensis* var. *tenebrionis*".

Ladd, Jr., *J. Econ. Entomol.*, 79, pp. 668–671 (1986) "Influence of Sugars on the Feeding Response of Japanese Beetles (Coleoptera: Scarabaeidae)".

Marrone et al., *J. Econ. Entomol.*, 78, pp. 290–293 (1985) "Improvements in Laboratory Rearing of the Southern Corn Rootworm, *Diabrotica undecimpuncta howardi* Barber (Coleoptera: Chrysomelidase), on an Aritificial Diet and Corn".

Krieg et al., *Anz. Schaedling., Pflanzenchutz, Umweltschutz*, 57, pp. 145–150 (1984) "Neue Ergebnisse uber *Bacillus thuringiensis* var. *tenebrionis* unter besonderer Berucksichtigung seiner Wirkung auf den Kartoffelkafer (*Leptinotarsa decemlineata*)".

Korn et al., *DNA*, 3, pp. 421–436, (1984) "Analysis of Biological Sequences on Small Computers".

Krieg et al., *A. Agnew. Ent.*, 96, pp. 500–508 (1983) (with translation) *Bacillus thuringiensis* var. *tenebrionis*: a new pathotype effective against larvae of Coleoptera.

Marinus et al., *Mol. Gen. Genet.*, 192, pp. 288–289 (1983) "Insertion Mutations in the dam Gene of *Escherichia coli* K-12".

Southern, *J. Molec. Biol.*, 98, pp. 503–517 (1975) "Detection of Specific sequences among DNA fragments separated by Gel Electrophoresis".

Daum, *Bull. Entomol. Soc. Am.*, 16, pp. 10–15 (1970) "Revision of two computer programs for Probit analysis".

Craigie, *J. Immunol.*, 21, pp. 417–511 (1936) "Studies on the serological reactions of the Flagella of *B. typhosus*".

Abbott, *J. Econ. Entomol.*, 18, pp. 265–267 (1925) "A method of computing the effectiveness of an insecticide".

cryIIIC(b) FIGURE 1A

```
         10         20         30         40         50         60
CCATATACAACTTATCAGGAAGGGGGGGATGCACAAAGAAGAAAAGAATAAGAAGTGAAT 70         80         90        100        110        120
GTTTATAATGTTCAATAGTTTTATGGGAAGGCATTTTATCAGGTAGAAAGTTATGTATTA 130        140        150        160        170        180
TGATAAGAATGGGAGGAAGAAAAATGAATCCAAACAATCGAAGTGAACATGATACGATAA
           RBS         MetAsnProAsnAsnArgSerGluHisAspThrIleL 190        200        210        220        230        240
AGGTTACACCTAACAGTGAATTGCCAACTAACCATAATCAATATCCTTTAGCTGACAATC
ysValThrProAsnSerGluLeuProThrAsnHisAsnGlnTyrProLeuAlaAspAsnP 250        260        270        280        290        300
CAAATTCGACACTAGAAGAATTAAATTATAAAGAATTTTTAAGAATGACTGAAGACAGTT
roAsnSerThrLeuGluGluLeuAsnTyrLysGluPheLeuArgMetThrGluAspSerS 310        320        330        340        350        360
CTACGGAAGTGCTAGACAACTCTACAGTAAAAGATGCAGTTGGGACAGGAATTTCTGTTG
erThrGluValLeuAspAsnSerThrValLysAspAlaValGlyThrGlyIleSerValV 370        380        390        400        410        420
TAGGGCAGATTTTAGGTGTTGTAGGAGTTCCATTTGCTGGGGCACTCACTTCATTTTATC
alGlyGlnIleLeuGlyValValGlyValProPheAlaGlyAlaLeuThrSerPheTyrG 430        440        450        460        470        480
AATCATTTCTTGACACTATATGGCCAAGTGATGCTGACCCATGGAAGGCTTTTATGGCAC
lnSerPheLeuAspThrIleTrpProSerAspAlaAspProTrpLysAlaPheMetAlaG 490        500        510        520        530        540
AAGTTGAAGTACTGATAGATAAGAAAATAGAGGAGTATGCTAAAAGTAAAGCTCTTGCAG
lnValGluValLeuIleAspLysLysIleGluGluTyrAlaLysSerLysAlaLeuAlaG 550        560        570        580        590        600
AGTTACAGGGTCTTCAAAATAATTTCGAAGATTATGTTAATGCGTTAAATTCCTGGAAGA
luLeuGlnGlyLeuGlnAsnAsnPheGluAspTyrValAsnAlaLeuAsnSerTrpLysL 610        620        630        640        650        660
AAACACCTTTAAGTTTGCGAAGTAAAAGAAGCCAAGATCGAATAAGGGAACTTTTTTCTC
ysThrProLeuSerLeuArgSerLysArgSerGlnAspArgIleArgGluLeuPheSerG 670        680        690        700        710        720
AAGCAGAAAGTCATTTTCGTAATTCCATGCCGTCATTTGCAGTTTCCAAATTCGAAGTGC
lnAlaGluSerHisPheArgAsnSerMetProSerPheAlaValSerLysPheGluValL 730        740        750        760        770        780
TGTTTCTACCAACATATGCACAAGCTGCAAATACACATTTATTGCTATTAAAAGATGCTC
euPheLeuProThrTyrAlaGlnAlaAlaAsnThrHisLeuLeuLeuLeuLysAspAlaG 790        800        810        820        830        840
AAGTTTTTGGAGAAGAATGGGGATATTCTTCAGAAGATGTTGCTGAATTTTATCATAGAC
lnValPheGlyGluGluTrpGlyTyrSerSerGluAspValAlaGluPheTyrHisArgG
```

FIGURE 1B

```
              850       860       870       880       890       900
     AATTAAAACTTACGCAACAATACACTGACCATTGTGTCAATTGGTATAATGTTGGATTAA
     lnLeuLysLeuThrGlnGlnTyrThrAspHisCysValAsnTrpTyrAsnValGlyLeuA 910       920       930       940       950       960
     ATGGTTTAAGAGGTTCAACTTATGATGCATGGGTCAAATTTAACCGTTTTCGCAGAGAAA
     snGlyLeuArgGlySerThrTyrAspAlaTrpValLysPheAsnArgPheArgArgGluM 970       980       990      1000      1010      1020
     TGACTTTAACTGTATTAGATCTAATTGTACTTTTCCCATTTTATGATGTTCGGTTATACT
     etThrLeuThrValLeuAspLeuIleValLeuPheProPheTyrAspValArgLeuTyrS 1030      1040      1050      1060      1070      1080
     CAAAAGGTGTTAAAACAGAACTAACAAGAGACATTTTTACGGATCCAATTTTTTCACTCA
     erLysGlyValLysThrGluLeuThrArgAspIlePheThrAspProIlePheSerLeuA 1090      1100      1110      1120      1130      1140
     ATACTCTTCAGGAGTATGGACCAACTTTTTTTGAGTATAGAAAACTCTATTCGAAAACCTC
     snThrLeuGlnGluTyrGlyProThrPheLeuSerIleGluAsnSerIleArgLysProH 1150      1160      1170      1180      1190      1200
     ATTTATTTGATTATTTACAGGGTATTGAATTTCATACGCGTCTTCAACCTGGTTACTCTG
     isLeuPheAspTyrLeuGlnGlyIleGluPheHisThrArgLeuGlnProGlyTyrSerG 1210      1220      1230      1240      1250      1260
     GGAAAGATTCTTTCAATTATTGGTCTGGTAATTATGTAGAAACTAGACCTAGTATAGGAT
     lyLysAspSerPheAsnTyrTrpSerGlyAsnTyrValGluThrArgProSerIleGlyS 1270      1280      1290      1300      1310      1320
     CTAGTAAGACAATTACTTCCCCATTTTATGGAGATAAATCTACTGAACCTGTACAAAAGT
     erSerLysThrIleThrSerProPheTyrGlyAspLysSerThrGluProValGlnLysL

HindIII
           / 1330      1340      1350      1360      1370      1380
     TAAGCTTTGATGGACAAAAAGTTTATCGAACTATAGCTAATACAGACGTAGCGGCTTGGC
     euSerPheAspGlyGlnLysValTyrArgThrIleAlaAsnThrAspValAlaAlaTrpP 1390      1400      1410      1420      1430      1440
     CGAATGGCAAGATATATTTTGGTGTTACGAAAGTTGATTTTAGTCAATATGATGATCAAA
     roAsnGlyLysIleTyrPheGlyValThrLysValAspPheSerGlnTyrAspAspGlnL 1450      1460      1470      1480      1490      1500
     AAAATGAAACTAGTACACAAACATATGATTCAAAAAGAAACAATGGCCATGTAGGTGCAC
     ysAsnGluThrSerThrGlnThrTyrAspSerLysArgAsnAsnGlyHisValGlyAlaG 1510      1520      1530      1540      1550      1560
     AGGATTCTATTGACCAATTACCACCAGAAACAACAGATGAACCACTTGAAAAAGCATATA
     lnAspSerIleAspGlnLeuProProGluThrThrAspGluProLeuGluLysAlaTyrS 1570      1580      1590      1600      1610      1620
     GTCATCAGCTTAATTACGCGGAATGTTTCTTAATGCAGGACCGTCGTGGAACAATTCCAT
     erHisGlnLeuAsnTyrAlaGluCysPheLeuMetGlnAspArgArgGlyThrIleProP 1630      1640      1650      1660      1670      1680
     TTTTTACTTGGACACATAGAAGTGTAGACTTTTTTAATACAATTGATGCTGAAAAGATTA
     hePheThrTrpThrHisArgSerValAspPhePheAsnThrIleAspAlaGluLysIleT
```

FIGURE 1C

```
          1690      1700      1710      1720      1730      1740
CTCAACTTCCAGTAGTGAAAGCATATGCCTTGTCTTCAGGTGCTTCCATTATTGAAGGTC
hrGlnLeuProValValLysAlaTyrAlaLeuSerSerGlyAlaSerIleIleGluGlyP 1750      1760      1770      1780      1790      1800
CAGGATTCACAGGAGGAAATTTACTATTCCTAAAAGAATCTAGTAATTCAATTGCTAAAT
roGlyPheThrGlyGlyAsnLeuLeuPheLeuLysGluSerSerAsnSerIleAlaLysP 1810      1820      1830      1840      1850      1860
TTAAAGTTACATTAAATTCAGCAGCCTTGTTACAACGATATCGTGTAAGAATACGCTATG
heLysValThrLeuAsnSerAlaAlaLeuLeuGlnArgTyrArgValArgIleArgTyrA 1870      1880      1890      1900      1910      1920
CTTCTACCACTAACTTACGACTTTTTGTGCAAAATTCAAACAATGATTTTATTGTCATCT
laSerThrThrAsnLeuArgLeuPheValGlnAsnSerAsnAsnAspPheIleValIleT 1930      1940      1950      1960      1970      1980
ACATTAATAAAACTATGAATATAGATGATGATTTAACATATCAAACATTTGATCTCGCAA
yrIleAsnLysThrMetAsnIleAspAspAspLeuThrTyrGlnThrPheAspLeuAlaT 1990      2000      2010      2020      2030      2040
CTACTAATTCTAATATGGGGTTCTCGGGTGATACGAATGAACTTATAATAGGAGCAGAAT
hrThrAsnSerAsnMetGlyPheSerGlyAspThrAsnGluLeuIleIleGlyAlaGluS 2050      2060      2070      2080      2090      2100
CTTTCGTTTCTAATGAAAAAATCTATATAGATAAGATAGAATTTATCCCAGTACAATTGT
erPheValSerAsnGluLysIleTyrIleAspLysIleGluPheIleProValGlnLeuE 2110      2120      2130      2140      2150      2160
AAGGAGATTTTGAAATGTAGGGCGATGGTCAAAATGAAAGAATAGGAAGGTGAATTTTGA
nd 2170      2180      2190      2200      2210      2220
TGGTTAGGAAAGATTCTTTTAAGAAAAGCAACATGGAAAAGTATACAGTACAAATATTAG 2230      2240      2250      2260      2270      2280
AAATAAAATTTATTAACACAGGGGAAGATGGTAAACCAGAACCGTATGGTTATATTGACT 2290      2300      2310      2320      2330      2340
TTTATTATCAACCTGCTCCTAACCTGAGAGAAGAAAAGTAAGAATTTGGGAAGAGAAAA 2350      2360      2370      2380      2390      2400
ATAGTAGCTCTCCACCTTCAATAGAAGTTATTACGGGGCTAACTTTTAATATCATGGCTA 2410      2420      2430
CTTCACTTAGCCGATTATGTTTTGAAGGTT
```

1 kb

Figure 7
1 2 3
70-  -70
30-  -30

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 2430 base pairs
        ( B ) TYPE: nucleic acid
        ( C ) STRANDEDNESS: double
        ( D ) TOPOLOGY: circular ( i i ) MOLECULE TYPE: DNA (genomic)

( i x ) FEATURE:
        ( A ) NAME/KEY: CDS
        ( B ) LOCATION: 144..2099

( x i ) SEQUENCE DESCRIPTION: SEQ ID NO:1:

```
CCATATACAA CTTATCAGGA AGGGGGGGAT GCACAAAGAA GAAAAGAATA AGAAGTGAAT      60

GTTTATAATG TTCAATAGTT TTATGGGAAG GCATTTATC  AGGTAGAAAG TTATGTATTA     120

TGATAAGAAT GGGAGGAAGA AAA ATG AAT CCA AAC AAT CGA AGT GAA CAT         170
                          Met Asn Pro Asn Asn Arg Ser Glu His
                            1               5

GAT ACG ATA AAG GTT ACA CCT AAC AGT GAA TTG CCA ACT AAC CAT AAT       218
Asp Thr Ile Lys Val Thr Pro Asn Ser Glu Leu Pro Thr Asn His Asn
 10              15                  20                  25

CAA TAT CCT TTA GCT GAC AAT CCA AAT TCG ACA CTA GAA GAA TTA AAT       266
Gln Tyr Pro Leu Ala Asp Asn Pro Asn Ser Thr Leu Glu Glu Leu Asn
                 30                  35                  40

TAT AAA GAA TTT TTA AGA ATG ACT GAA GAC AGT TCT ACG GAA GTG CTA       314
Tyr Lys Glu Phe Leu Arg Met Thr Glu Asp Ser Ser Thr Glu Val Leu
             45                  50                  55

GAC AAC TCT ACA GTA AAA GAT GCA GTT GGG ACA GGA ATT TCT GTT GTA       362
Asp Asn Ser Thr Val Lys Asp Ala Val Gly Thr Gly Ile Ser Val Val
         60                  65                  70

GGG CAG ATT TTA GGT GTT GTA GGA GTT CCA TTT GCT GGG GCA CTC ACT       410
Gly Gln Ile Leu Gly Val Val Gly Val Pro Phe Ala Gly Ala Leu Thr
     75                  80                  85

TCA TTT TAT CAA TCA TTT CTT GAC ACT ATA TGG CCA AGT GAT GCT GAC       458
Ser Phe Tyr Gln Ser Phe Leu Asp Thr Ile Trp Pro Ser Asp Ala Asp
 90                  95                 100                 105

CCA TGG AAG GCT TTT ATG GCA CAA GTT GAA GTA CTG ATA GAT AAG AAA       506
Pro Trp Lys Ala Phe Met Ala Gln Val Glu Val Leu Ile Asp Lys Lys
                110                 115                 120

ATA GAG GAG TAT GCT AAA AGT AAA GCT CTT GCA GAG TTA CAG GGT CTT       554
Ile Glu Glu Tyr Ala Lys Ser Lys Ala Leu Ala Glu Leu Gln Gly Leu
            125                 130                 135

CAA AAT AAT TTC GAA GAT TAT GTT AAT GCG TTA AAT TCC TGG AAG AAA       602
Gln Asn Asn Phe Glu Asp Tyr Val Asn Ala Leu Asn Ser Trp Lys Lys
        140                 145                 150

ACA CCT TTA AGT TTG CGA AGT AAA AGA AGC CAA GAT CGA ATA AGG GAA       650
Thr Pro Leu Ser Leu Arg Ser Lys Arg Ser Gln Asp Arg Ile Arg Glu
    155                 160                 165

CTT TTT TCT CAA GCA GAA AGT CAT TTT CGT AAT TCC ATG CCG TCA TTT       698
Leu Phe Ser Gln Ala Glu Ser His Phe Arg Asn Ser Met Pro Ser Phe
170                 175                 180                 185

GCA GTT TCC AAA TTC GAA GTG CTG TTT CTA CCA ACA TAT GCA CAA GCT       746
Ala Val Ser Lys Phe Glu Val Leu Phe Leu Pro Thr Tyr Ala Gln Ala
                190                 195                 200

GCA AAT ACA CAT TTA TTG CTA TTA AAA GAT GCT CAA GTT TTT GGA GAA       794
```

|     |     |     |     |     |     |     |     |     |     |     |     |     |     |     |     |
|---|---|---|---|---|---|---|---|---|---|---|---|---|---|---|---|
| Ala | Asn | Thr | His<br>205 | Leu | Leu | Leu | Leu | Lys<br>210 | Asp | Ala | Gln | Val<br>215 | Phe | Gly | Glu |

| GAA | TGG | GGA | TAT | TCT | TCA | GAA | GAT | GTT | GCT | GAA | TTT | TAT | CAT | AGA | CAA | 842 |
|---|---|---|---|---|---|---|---|---|---|---|---|---|---|---|---|---|
| Glu | Trp | Gly<br>220 | Tyr | Ser | Ser | Glu<br>225 | Asp | Val | Ala | Glu | Phe | Tyr<br>230 | His | Arg | Gln | |

| TTA | AAA | CTT | ACG | CAA | CAA | TAC | ACT | GAC | CAT | TGT | GTC | AAT | TGG | TAT | AAT | 890 |
|---|---|---|---|---|---|---|---|---|---|---|---|---|---|---|---|---|
| Leu | Lys<br>235 | Leu | Thr | Gln | Gln | Tyr<br>240 | Thr | Asp | His | Cys | Val<br>245 | Asn | Trp | Tyr | Asn | |

| GTT | GGA | TTA | AAT | GGT | TTA | AGA | GGT | TCA | ACT | TAT | GAT | GCA | TGG | GTC | AAA | 938 |
|---|---|---|---|---|---|---|---|---|---|---|---|---|---|---|---|---|
| Val<br>250 | Gly | Leu | Asn | Gly | Leu<br>255 | Arg | Gly | Ser | Thr | Tyr<br>260 | Asp | Ala | Trp | Val | Lys<br>265 | |

| TTT | AAC | CGT | TTT | CGC | AGA | GAA | ATG | ACT | TTA | ACT | GTA | TTA | GAT | CTA | ATT | 986 |
|---|---|---|---|---|---|---|---|---|---|---|---|---|---|---|---|---|
| Phe | Asn | Arg | Phe | Arg<br>270 | Arg | Glu | Met | Thr | Leu<br>275 | Thr | Val | Leu | Asp<br>280 | Leu | Ile | |

| GTA | CTT | TTC | CCA | TTT | TAT | GAT | GTT | CGG | TTA | TAC | TCA | AAA | GGT | GTT | AAA | 1034 |
|---|---|---|---|---|---|---|---|---|---|---|---|---|---|---|---|---|
| Val | Leu | Phe | Pro<br>285 | Phe | Tyr | Asp | Val | Arg<br>290 | Leu | Tyr | Ser | Lys | Gly<br>295 | Val | Lys | |

| ACA | GAA | CTA | ACA | AGA | GAC | ATT | TTT | ACG | GAT | CCA | ATT | TTT | TCA | CTC | AAT | 1082 |
|---|---|---|---|---|---|---|---|---|---|---|---|---|---|---|---|---|
| Thr | Glu | Leu<br>300 | Thr | Arg | Asp | Ile | Phe<br>305 | Thr | Asp | Pro | Ile | Phe<br>310 | Ser | Leu | Asn | |

| ACT | CTT | CAG | GAG | TAT | GGA | CCA | ACT | TTT | TTG | AGT | ATA | GAA | AAC | TCT | ATT | 1130 |
|---|---|---|---|---|---|---|---|---|---|---|---|---|---|---|---|---|
| Thr | Leu | Gln | Glu<br>315 | Tyr | Gly | Pro | Thr | Phe<br>320 | Leu | Ser | Ile | Glu | Asn<br>325 | Ser | Ile | |

| CGA | AAA | CCT | CAT | TTA | TTT | GAT | TAT | TTA | CAG | GGT | ATT | GAA | TTT | CAT | ACG | 1178 |
|---|---|---|---|---|---|---|---|---|---|---|---|---|---|---|---|---|
| Arg<br>330 | Lys | Pro | His | Leu | Phe<br>335 | Asp | Tyr | Leu | Gln | Gly<br>340 | Ile | Glu | Phe | His | Thr<br>345 | |

| CGT | CTT | CAA | CCT | GGT | TAC | TCT | GGG | AAA | GAT | TCT | TTC | AAT | TAT | TGG | TCT | 1226 |
|---|---|---|---|---|---|---|---|---|---|---|---|---|---|---|---|---|
| Arg | Leu | Gln | Pro | Gly<br>350 | Tyr | Ser | Gly | Lys | Asp<br>355 | Ser | Phe | Asn | Tyr | Trp<br>360 | Ser | |

| GGT | AAT | TAT | GTA | GAA | ACT | AGA | CCT | AGT | ATA | GGA | TCT | AGT | AAG | ACA | ATT | 1274 |
|---|---|---|---|---|---|---|---|---|---|---|---|---|---|---|---|---|
| Gly | Asn | Tyr | Val<br>365 | Glu | Thr | Arg | Pro | Ser<br>370 | Ile | Gly | Ser | Ser | Lys<br>375 | Thr | Ile | |

| ACT | TCC | CCA | TTT | TAT | GGA | GAT | AAA | TCT | ACT | GAA | CCT | GTA | CAA | AAG | TTA | 1322 |
|---|---|---|---|---|---|---|---|---|---|---|---|---|---|---|---|---|
| Thr | Ser | Pro<br>380 | Phe | Tyr | Gly | Asp | Lys<br>385 | Ser | Thr | Glu | Pro | Val<br>390 | Gln | Lys | Leu | |

| AGC | TTT | GAT | GGA | CAA | AAA | GTT | TAT | CGA | ACT | ATA | GCT | AAT | ACA | GAC | GTA | 1370 |
|---|---|---|---|---|---|---|---|---|---|---|---|---|---|---|---|---|
| Ser | Phe<br>395 | Asp | Gly | Gln | Lys | Val<br>400 | Tyr | Arg | Thr | Ile | Ala<br>405 | Asn | Thr | Asp | Val | |

| GCG | GCT | TGG | CCG | AAT | GGC | AAG | ATA | TAT | TTT | GGT | GTT | ACG | AAA | GTT | GAT | 1418 |
|---|---|---|---|---|---|---|---|---|---|---|---|---|---|---|---|---|
| Ala<br>410 | Ala | Trp | Pro | Asn | Gly<br>415 | Lys | Ile | Tyr | Phe | Gly<br>420 | Val | Thr | Lys | Val | Asp<br>425 | |

| TTT | AGT | CAA | TAT | GAT | GAT | CAA | AAA | AAT | GAA | ACT | AGT | ACA | CAA | ACA | TAT | 1466 |
|---|---|---|---|---|---|---|---|---|---|---|---|---|---|---|---|---|
| Phe | Ser | Gln | Tyr | Asp<br>430 | Asp | Gln | Lys | Asn | Glu<br>435 | Thr | Ser | Thr | Gln | Thr<br>440 | Tyr | |

| GAT | TCA | AAA | AGA | AAC | AAT | GGC | CAT | GTA | GGT | GCA | CAG | GAT | TCT | ATT | GAC | 1514 |
|---|---|---|---|---|---|---|---|---|---|---|---|---|---|---|---|---|
| Asp | Ser | Lys | Arg<br>445 | Asn | Asn | Gly | His | Val<br>450 | Gly | Ala | Gln | Asp | Ser<br>455 | Ile | Asp | |

| CAA | TTA | CCA | CCA | GAA | ACA | ACA | GAT | GAA | CCA | CTT | GAA | AAA | GCA | TAT | AGT | 1562 |
|---|---|---|---|---|---|---|---|---|---|---|---|---|---|---|---|---|
| Gln | Leu | Pro<br>460 | Pro | Glu | Thr | Thr | Asp<br>465 | Glu | Pro | Leu | Glu | Lys<br>470 | Ala | Tyr | Ser | |

| CAT | CAG | CTT | AAT | TAC | GCG | GAA | TGT | TTC | TTA | ATG | CAG | GAC | CGT | CGT | GGA | 1610 |
|---|---|---|---|---|---|---|---|---|---|---|---|---|---|---|---|---|
| His | Gln | Leu | Asn<br>475 | Tyr | Ala | Glu | Cys | Phe<br>480 | Leu | Met | Gln | Asp | Arg<br>485 | Arg | Gly | |

| ACA | ATT | CCA | TTT | TTT | ACT | TGG | ACA | CAT | AGA | AGT | GTA | GAC | TTT | TTT | AAT | 1658 |
|---|---|---|---|---|---|---|---|---|---|---|---|---|---|---|---|---|
| Thr<br>490 | Ile | Pro | Phe | Phe | Thr<br>495 | Trp | Thr | His | Arg | Ser<br>500 | Val | Asp | Phe | Phe | Asn<br>505 | |

| ACA | ATT | GAT | GCT | GAA | AAG | ATT | ACT | CAA | CTT | CCA | GTA | GTG | AAA | GCA | TAT | 1706 |
|---|---|---|---|---|---|---|---|---|---|---|---|---|---|---|---|---|
| Thr | Ile | Asp | Ala | Glu<br>510 | Lys | Ile | Thr | Gln | Leu<br>515 | Pro | Val | Val | Lys | Ala<br>520 | Tyr | |

| GCC | TTG | TCT | TCA | GGT | GCT | TCC | ATT | ATT | GAA | GGT | CCA | GGA | TTC | ACA | GGA | 1754 |
|---|---|---|---|---|---|---|---|---|---|---|---|---|---|---|---|---|
| Ala | Leu | Ser | Ser<br>525 | Gly | Ala | Ser | Ile | Ile<br>530 | Glu | Gly | Pro | Gly | Phe<br>535 | Thr | Gly | |

-continued

| | | | | | | | | | | | | | | | | |
|---|---|---|---|---|---|---|---|---|---|---|---|---|---|---|---|---|
| GGA | AAT | TTA | CTA | TTC | CTA | AAA | GAA | TCT | AGT | AAT | TCA | ATT | GCT | AAA | TTT | 1802 |
| Gly | Asn | Leu | Leu | Phe | Leu | Lys | Glu | Ser | Ser | Asn | Ser | Ile | Ala | Lys | Phe | |
| | | | 540 | | | | 545 | | | | | 550 | | | | |
| AAA | GTT | ACA | TTA | AAT | TCA | GCA | GCC | TTG | TTA | CAA | CGA | TAT | CGT | GTA | AGA | 1850 |
| Lys | Val | Thr | Leu | Asn | Ser | Ala | Ala | Leu | Leu | Gln | Arg | Tyr | Arg | Val | Arg | |
| | | 555 | | | | | 560 | | | | 565 | | | | | |
| ATA | CGC | TAT | GCT | TCT | ACC | ACT | AAC | TTA | CGA | CTT | TTT | GTG | CAA | AAT | TCA | 1898 |
| Ile | Arg | Tyr | Ala | Ser | Thr | Thr | Asn | Leu | Arg | Leu | Phe | Val | Gln | Asn | Ser | |
| 570 | | | | | 575 | | | | | 580 | | | | | 585 | |
| AAC | AAT | GAT | TTT | ATT | GTC | ATC | TAC | ATT | AAT | AAA | ACT | ATG | AAT | ATA | GAT | 1946 |
| Asn | Asn | Asp | Phe | Ile | Val | Ile | Tyr | Ile | Asn | Lys | Thr | Met | Asn | Ile | Asp | |
| | | | | 590 | | | | | 595 | | | | | 600 | | |
| GAT | GAT | TTA | ACA | TAT | CAA | ACA | TTT | GAT | CTC | GCA | ACT | ACT | AAT | TCT | AAT | 1994 |
| Asp | Asp | Leu | Thr | Tyr | Gln | Thr | Phe | Asp | Leu | Ala | Thr | Thr | Asn | Ser | Asn | |
| | | | 605 | | | | 610 | | | | | 615 | | | | |
| ATG | GGG | TTC | TCG | GGT | GAT | ACG | AAT | GAA | CTT | ATA | ATA | GGA | GCA | GAA | TCT | 2042 |
| Met | Gly | Phe | Ser | Gly | Asp | Thr | Asn | Glu | Leu | Ile | Ile | Gly | Ala | Glu | Ser | |
| | | 620 | | | | | 625 | | | | | 630 | | | | |
| TTC | GTT | TCT | AAT | GAA | AAA | ATC | TAT | ATA | GAT | AAG | ATA | GAA | TTT | ATC | CCA | 2090 |
| Phe | Val | Ser | Asn | Glu | Lys | Ile | Tyr | Ile | Asp | Lys | Ile | Glu | Phe | Ile | Pro | |
| | 635 | | | | | 640 | | | | | 645 | | | | | |
| GTA | CAA | TTG | TAAGGAGATT | TTGAAATGTA | GGGCGATGGT | CAAAATGAAA | | | | | | | | | | 2139 |
| Val | Gln | Leu | | | | | | | | | | | | | | |
| 650 | | | | | | | | | | | | | | | | |

GAATAGGAAG GTGAATTTTG ATGGTTAGGA AAGATTCTTT TAAGAAAAGC AACATGGAAA 2199

AGTATACAGT ACAAATATTA GAAATAAAAT TTATTAACAC AGGGGAAGAT GGTAAACCAG 2259

AACCGTATGG TTATATTGAC TTTTATTATC AACCTGCTCC TAACCTGAGA GAAGAAAAG 2319

TAAGAATTTG GAAGAGAAA AATAGTAGCT CTCCACCTTC AATAGAAGTT ATTACGGGGC 2379

TAACTTTTAA TATCATGGCT ACTTCACTTA GCCGATTATG TTTTGAAGGT T 2430

( 2 ) INFORMATION FOR SEQ ID NO:2:

( i ) SEQUENCE CHARACTERISTICS:
        ( A ) LENGTH: 652 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Met | Asn | Pro | Asn | Asn | Arg | Ser | Glu | His | Asp | Thr | Ile | Lys | Val | Thr | Pro |
| 1 | | | | 5 | | | | | 10 | | | | | 15 | |
| Asn | Ser | Glu | Leu | Pro | Thr | Asn | His | Asn | Gln | Tyr | Pro | Leu | Ala | Asp | Asn |
| | | | 20 | | | | | 25 | | | | | 30 | | |
| Pro | Asn | Ser | Thr | Leu | Glu | Glu | Leu | Asn | Tyr | Lys | Glu | Phe | Leu | Arg | Met |
| | | | 35 | | | | 40 | | | | | 45 | | | |
| Thr | Glu | Asp | Ser | Ser | Thr | Glu | Val | Leu | Asp | Asn | Ser | Thr | Val | Lys | Asp |
| | 50 | | | | | 55 | | | | | 60 | | | | |
| Ala | Val | Gly | Thr | Gly | Ile | Ser | Val | Val | Gly | Gln | Ile | Leu | Gly | Val | Val |
| 65 | | | | | 70 | | | | | 75 | | | | | 80 |
| Gly | Val | Pro | Phe | Ala | Gly | Ala | Leu | Thr | Ser | Phe | Tyr | Gln | Ser | Phe | Leu |
| | | | | 85 | | | | | 90 | | | | | 95 | |
| Asp | Thr | Ile | Trp | Pro | Ser | Asp | Ala | Asp | Pro | Trp | Lys | Ala | Phe | Met | Ala |
| | | | | 100 | | | | | 105 | | | | | 110 | |
| Gln | Val | Glu | Val | Leu | Ile | Asp | Lys | Lys | Ile | Glu | Glu | Tyr | Ala | Lys | Ser |
| | | | 115 | | | | | 120 | | | | | 125 | | |
| Lys | Ala | Leu | Ala | Glu | Leu | Gln | Gly | Leu | Gln | Asn | Asn | Phe | Glu | Asp | Tyr |
| | 130 | | | | | 135 | | | | | 140 | | | | |

```
Val  Asn  Ala  Leu  Asn  Ser  Trp  Lys  Lys  Thr  Pro  Leu  Ser  Leu  Arg  Ser
145                 150                      155                      160

Lys  Arg  Ser  Gln  Asp  Arg  Ile  Arg  Glu  Leu  Phe  Ser  Gln  Ala  Glu  Ser
                165                      170                      175

His  Phe  Arg  Asn  Ser  Met  Pro  Ser  Phe  Ala  Val  Ser  Lys  Phe  Glu  Val
               180                      185                      190

Leu  Phe  Leu  Pro  Thr  Tyr  Ala  Gln  Ala  Ala  Asn  Thr  His  Leu  Leu  Leu
               195                      200                      205

Leu  Lys  Asp  Ala  Gln  Val  Phe  Gly  Glu  Glu  Trp  Gly  Tyr  Ser  Ser  Glu
          210                      215                      220

Asp  Val  Ala  Glu  Phe  Tyr  His  Arg  Gln  Leu  Lys  Leu  Thr  Gln  Gln  Tyr
225                      230                      235                      240

Thr  Asp  His  Cys  Val  Asn  Trp  Tyr  Asn  Val  Gly  Leu  Asn  Gly  Leu  Arg
               245                      250                      255

Gly  Ser  Thr  Tyr  Asp  Ala  Trp  Val  Lys  Phe  Asn  Arg  Phe  Arg  Arg  Glu
               260                      265                      270

Met  Thr  Leu  Thr  Val  Leu  Asp  Leu  Ile  Val  Leu  Phe  Pro  Phe  Tyr  Asp
               275                      280                      285

Val  Arg  Leu  Tyr  Ser  Lys  Gly  Val  Lys  Thr  Glu  Leu  Thr  Arg  Asp  Ile
     290                      295                      300

Phe  Thr  Asp  Pro  Ile  Phe  Ser  Leu  Asn  Thr  Leu  Gln  Glu  Tyr  Gly  Pro
305                      310                      315                      320

Thr  Phe  Leu  Ser  Ile  Glu  Asn  Ser  Ile  Arg  Lys  Pro  His  Leu  Phe  Asp
                325                      330                      335

Tyr  Leu  Gln  Gly  Ile  Glu  Phe  His  Thr  Arg  Leu  Gln  Pro  Gly  Tyr  Ser
               340                      345                      350

Gly  Lys  Asp  Ser  Phe  Asn  Tyr  Trp  Ser  Gly  Asn  Tyr  Val  Glu  Thr  Arg
          355                      360                      365

Pro  Ser  Ile  Gly  Ser  Ser  Lys  Thr  Ile  Thr  Ser  Pro  Phe  Tyr  Gly  Asp
     370                      375                      380

Lys  Ser  Thr  Glu  Pro  Val  Gln  Lys  Leu  Ser  Phe  Asp  Gly  Gln  Lys  Val
385                      390                      395                      400

Tyr  Arg  Thr  Ile  Ala  Asn  Thr  Asp  Val  Ala  Ala  Trp  Pro  Asn  Gly  Lys
                405                      410                      415

Ile  Tyr  Phe  Gly  Val  Thr  Lys  Val  Asp  Phe  Ser  Gln  Tyr  Asp  Asp  Gln
               420                      425                      430

Lys  Asn  Glu  Thr  Ser  Thr  Gln  Thr  Tyr  Asp  Ser  Lys  Arg  Asn  Asn  Gly
          435                      440                      445

His  Val  Gly  Ala  Gln  Asp  Ser  Ile  Asp  Gln  Leu  Pro  Pro  Glu  Thr  Thr
     450                      455                      460

Asp  Glu  Pro  Leu  Glu  Lys  Ala  Tyr  Ser  His  Gln  Leu  Asn  Tyr  Ala  Glu
465                      470                      475                      480

Cys  Phe  Leu  Met  Gln  Asp  Arg  Arg  Gly  Thr  Ile  Pro  Phe  Phe  Thr  Trp
               485                      490                      495

Thr  His  Arg  Ser  Val  Asp  Phe  Phe  Asn  Thr  Ile  Asp  Ala  Glu  Lys  Ile
               500                      505                      510

Thr  Gln  Leu  Pro  Val  Val  Lys  Ala  Tyr  Ala  Leu  Ser  Ser  Gly  Ala  Ser
          515                      520                      525

Ile  Ile  Glu  Gly  Pro  Gly  Phe  Thr  Gly  Gly  Asn  Leu  Leu  Phe  Leu  Lys
     530                      535                      540

Glu  Ser  Ser  Asn  Ser  Ile  Ala  Lys  Phe  Lys  Val  Thr  Leu  Asn  Ser  Ala
545                      550                      555                      560

Ala  Leu  Leu  Gln  Arg  Tyr  Arg  Val  Arg  Ile  Arg  Tyr  Ala  Ser  Thr  Thr
               565                      570                      575

Asn  Leu  Arg  Leu  Phe  Val  Gln  Asn  Ser  Asn  Asn  Asp  Phe  Ile  Val  Ile
```

```
                        580                           585                              590
Tyr  Ile  Asn  Lys  Thr  Met  Asn  Ile  Asp  Asp  Asp  Leu  Thr  Tyr  Gln  Thr
               595                      600                 605

Phe  Asp  Leu  Ala  Thr  Thr  Asn  Ser  Asn  Met  Gly  Phe  Ser  Gly  Asp  Thr
     610                      615                      620

Asn  Glu  Leu  Ile  Ile  Gly  Ala  Glu  Ser  Phe  Val  Ser  Asn  Glu  Lys  Ile
625                      630                     635                          640

Tyr  Ile  Asp  Lys  Ile  Glu  Phe  Ile  Pro  Val  Gln  Leu
                    645                      650
```

BACILLUS THURINGIENSIS CRYIIIC(B) TOXIN GENE AND PROTEIN TOXIC TO COLEOPTERAN INSECTS

Cross-Reference to Related Applications

This application is a continuation of copending U.S. patent application 07/813,592, filed Dec. 23, 1991, now abandoned, which was a continuation-in-part of copending U.S. patent application Ser. No. 07/649,562, filed Jan. 31, 1991.

FIELD OF THE INVENTION

The present invention relates to an isolated *Bacillus thuringiensis* strain, to its novel toxin encoding gene and to the insecticidal crystal protein toxin made by the gene, as well as to insecticidal compositions containing the protein that are toxic to coleopteran insects.

BACKGROUND OF THE INVENTION

*Bacillus thuringiensis* (hereinafter "B.t.") is a gram-positive soil bacterium that produces crystal proteins during sporulation which are specifically toxic to certain orders and species of insects. Many different strains of B.t. have been shown to produce insecticidal crystal proteins. Compositions including B.t. strains which produce insecticidal proteins have been commercially available and used as environmentally acceptable insecticides because they are quite toxic to the specific target insect, but are harmless to plants and other non-targeted organisms.

A number of genes encoding crystal proteins have been cloned from several strains of B.t. A review of such genes is set forth in H. Höfte et al., Microbiol. Rev., 53, pp.242-255 (1989). This reference provides a good overview of the genes and proteins obtained from B.t. and their uses, adopts a nomenclature and classification scheme for B.t. genes and proteins, and has an extensive bibliography.

The B.t. crystal protein is toxic in the insect only after ingestion. After ingestion, the alkaline pH and proteolytic enzymes in the insect mid-gut solubilize the crystal allowing the release of the toxic components. These toxic components disrupt the mid-gut cells causing the insect to cease feeding and, eventually, to die. In fact, B.t. has proven to be an effective and environmentally safe insecticide in dealing with various insect pests.

As noted by Hdfte et al., the majority of insecticidal B.t. strains are active against insects of the order Lepidoptera, i.e., caterpillar insects. Other B.t. strains are insecticidally active against insects of the order Diptera, i.e., flies and mosquitoes, or against both lepidopteran and dipteran insects. In recent years, a few B.t. strains have been reported as producing crystal protein that is toxic to insects of the order Coleoptera, i.e., beetles.

The first isolation of a coleopteran-toxic B.t. strain is reported by A. Krieg et al., in *Z.angew.Ent.*, 96, pp.500-508 (1983); see also A. Krieg et al., *Anz.Schaedlingskde., Pflanzenschutz, Umweltschutz*, 57, pp.145-150 (1984) and U.S. Pat. No. 4,766,203, issued Aug. 23, 1988 of A. Krieg et al. The strain, designated B.t. var. tenebrionis, is reported to be toxic to larvae of the coleopteran insects *Agelastica alni* (blue alder leaf beetle) and *Leptinotarsa decemlineata* (Colorado potato beetle). *B.t. tenebrionis* makes an insecticidal crystal protein reported to be about 65-70 kilodaltons (kDa) (U.S. Pat. No. 4,766,203; see also K. Bernhard, *FEMS Microbiol.Lett.*, 33, pp.261-265 (1986)).

V. Sekar et al., *Proc.Natl.Acad.Sci.USA*, 84, pp.7036-7040 (1987), report the cloning and characterization of the gene for the coleopteran-toxic crystal protein of *B.t. tenebrionis*. The size of the protein, as deduced from the sequence of the gene, was 73 kDa, but the isolated protein contained primarily a 65 kDa component. Höfte et al., *Nucleic Acids Res.*, 15, p.7183 (1987), also report the DNA sequence for the cloned gene from *B.t. tenebrionis*, and the sequence of the gene is identical to that reported by Sekar et al. (1987).

McPherson et al., *Bio/Technology*, 6, pp.61-66 (1988), disclose the DNA sequence for the cloned insect control gene from *B.t. tenebrionis*, and the sequence is identical to that reported by Sekar et al. (1987). *E.coli* cells and *Pseudomonas fluorescens* cells harboring the cloned gene were found to be toxic to Colorado potato beetle larvae.

PCT International Publication No. WO 91/07481 dated May 30, 1991, of Novo Nordisk A/S, describes B.t. mutants that produce high yields of the same insecticidal proteins originally made by the parent strains at lesser yields. Mutants of the coleopteran-toxic *B.t. tenebrionis* strain are disclosed.

A coleopteran-toxic strain, designated *B.t.* var. *san diego*, is reported by C. Herrnstadt et al., Bio/Technology, 4, pp.305-308 (1986), to produce a 64 kDa crystal protein that was toxic to various coleopteran insects: strong toxicity to *Pyrrhalta luteola* (elm leaf beetle); moderate toxicity to *Anthonomus grandis* (boll weevil), *Leptinotarsa decemlineata* (Colorado potato beetle), *Otiorhynchus sulcatus* (black vine weevil), *Tenebrio molitor* (yellow mealworm) and *Haltica tombacina;* and weak toxicity to *Diabrotica undecimpunctata undecimpunctata* (western spotted cucumber beetle).

The DNA sequence of the cloned coleopteran toxin gene of *B.t. san diego* is reported in C. Herrnstadt et al., *Gene*, 57, pp.37-46 (1987); see also U.S. Pat. No. 4,771,131, issued Sep. 13, 1988, of Herrnstadt et al. The sequence of the toxin gene of *B.t. san diego* is identical to that reported by Sear et al. (1987) for the cloned coleopteran toxin gene of *B.t. tenebrionis*.

A. Krieg et al., J.Appl.Ent., 104, pp.417-424 (1987), report that the strain B.t. san diego is identical to the *B.t. tenebrionis* strain, based on various diagnostic tests.

Another new B.t. strain, designated EG2158, is reported by W. P. Donovan et al., in *Mol.Gen.Genet.*, 214, pp.365-372 (1988) and in U.S. Pat. No. 5,024,837 issued Jun. 18, 1991, to produce a 73 kDa crystal protein that is insecticidal to coleopteran insects. The toxin-encoding gene from B.t. strain EG2158 was cloned and sequenced, and its sequence is identical to that reported by Sekar et al. (1987) for the cloned *B.t. tenebrionis* coleopteran toxin gene. This coleopteran toxin gene is referred to as the cryIIIA gene by Höfte et al., *Microbiol.Rev.*, 53, pp.242-255 (1989).

The Donovan et al. '837 U.S. patent noted above also describes hybrid *B.t.* var. *kurstaki* strains designated EG2424 and EG2421, which are active against both lepidopteran insects and coleopteran insects. The beetle activity of these hybrid strains results from the coleopteran toxin plasmid transferred from B.t. strain EG2158 by conjugal plasmid transfer.

U.S. Pat. No. 4,797,279, issued Jan. 10, 1989, of D. Karamata et al. (corresponding to EP-A-0 221 024), discloses a hybrid B.t. microorganism containing a plasmid from B.t. var. kurstaki with a lepidopteran toxin gene and a plasmid from *B.t. tenebrionis* with a ooleopteran toxin gene. The hybrid B.t. produces crystal proteins characteristic of those made by *B.t. kurstaki*, as well as those of *B.t. tenebrionis*.

U.S. Pat. No. 4,910,016, issued Mar. 20, 1990, of Gaertner et al. (corresponding to EP-A-0 303 379), discloses a novel B.t. isolate identified as B.t. MT 104 which has insecticidal activity against two orders of insects, Colorado potato beetle (Coleoptera) and cabbage looper (Lepidoptera).

European Patent Application Publication No. 0 318 143, published May 31, 1989, of Lubrizol Genetics, Inc., discloses the cloning, characterization and selective expression of the intact partially modified gene from *B.t. tenebrionis*, and the transfer of the cloned gene into a host microorganism rendering the microorganism able to produce a protein having toxicity to coleopteran insects. Insect bioassay data for B.t. san diego reproduced from Herrnstadt et al., *Bio/Technology*, 4, pp.305-308 (1986) discussed above, is summarized. The summary also includes data for *B.t. tenebrionis* from another source; *B.t. tenebrionis* is reported to exhibit strong toxicity to Colorado potato beetle, moderate toxicity to western corn rootworm (*Diabrotica virgifera*) and weak toxicity to southern corn rootworm (*Diabrotica undecimpunctata*).

European Patent Application Publication No. 0 324 254, published Jul. 19, 1989, of Imperial Chemical Industries PLC, discloses a novel B.t. strain identified as A30 which has insecticidal activity against coleopteran insects, including Colorado potato beetle larvae, corn rootworm larvae and boll weevils.

U.S. Pat. No. 4,999,192, issued Mar. 12, 1991, of Payne et al. (corresponding to EP A-0 328 383), discloses a novel B.t. microorganism identified as B.t. PS40D1 which has insecticidal activity against Colorado potato beetle larvae. B.t. strain PS40DI is identified via serotyping as being serovar 8a8b, morrisoni.

U.S. Pat. No. 5,006,336, issued Apr. 9, 1991, of Payne et al. (corresponding to EP-A-0 346 114), discloses a novel B.t. isolate designated as PS122D3, which is serotyped as serovar 8a8b, morrisoni and which exhibits insecticidal activity against Colorado potato beetle larvae.

U.S. Pat. No. 4,966,765, issued Oct. 30, 1990, of Payne et al. (corresponding to EP-A-0 330 342), discloses a novel B.t. microorganism identified as B.t. PS86B1 which has insecticidal activity against the Colorado potato beetle. B.t. strain PS86B1 is identified via serotyping as being serovar tolworthi.

The nucleotide sequence of a cryIIIB gene and its encoded coleopteran-toxic protein is reported by Sick et al., in *Nucleic Acids Res.*, 18, p.1305 (1990) but the B.t. source strain is identified only via serotyping as being subspecies tolworthi. U.S. Pat. No. 4,966,155, issued Feb. 26, 1991, of Sick et al. (corresponding to EP-A-0 337 604), discloses a B.t. toxin gene obtained from the coleopteran-active B.t. strain 43F, and the gene sequence appears identical to the cryIIIB gene. B.t. strain 43F is reported as being active against Colorado potato beetle and *Leptinotarsa texana*.

European Patent Application No. 0 382 990, published Aug. 22, 1990, of Plant Genetic Systems N.V., discloses two novel B.t. strains (btPGSI208 and btPGSI245) producing respective crystal proteins of 74 and 129 kDa that exhibit insecticidal activity against Colorado potato beetle larvae. The DNA sequence reported for toxin gene producing the 74 kDa protein appears to be related to that of the cryIIIB gene of Sick et al.

PCT International Publication No. WO 90/13651, published Nov. 15, 1990, of Imperial Chemical Industries PLC, discloses novel B.t. strains which contain a toxin gene encoding an 81 kDa protein that is stated to be toxic not only to lepidopteran insects but also to coleopteran insects, including Diabrotica.

U.S. Pat. No. 5,055,293, issued Oct. 8, 1991, of Aronson et al., discloses the use of B. laterosporous for corn rootworm (Diabrotica) insect control.

The various B.t. strains described in aforementioned literature are reported to have crystal proteins insecticidally active against coleopteran insects, but none has been demonstrated to have significant, quantifiable toxicity to the larvae and adults of the insect genus Diabrotica (corn rootworm), which includes the western corn rootworm (*Diabrotica virgifera virgifera*), the southern corn rootworm (*Diabrotica undecimpunctata howardi*) and the northern corn rootworm (*Diabrotica barberi*).

The B.t. strain of the present invention contains a novel toxin gene that expresses protein toxin having quantifiable insecticidal activity against the Diabrotica insects, among other coleopteran insects.

SUMMARY OF THE INVENTION

One aspect of the present invention relates to a purified and isolated coleopteran toxin gene having a nucleotide base sequence coding for the amino acid sequence illustrated in FIG. 1 and hereinafter designated as the cryIIIC(b) gene (SEQ ID NO:1). The cryIIIC(b) gene (SEQ ID NO:1) has a coding region extending from nucleotide bases 144 to 2099 shown in FIG. 1.

Another aspect of the present invention relates to the insecticidal protein produced by the cryIIIC(b) gene. The CryIIIC(b) protein (SEQ ID NO:2) has the amino acid sequence, as deduced from the nucleotide sequence of the cryIIIC(b) gene (SEQ ID NO:1) from nucleotide bases 144 to 2099 that is shown in FIG. 1. The protein exhibits insecticidal activity against insects of the order Coleoptera, in particular, Colorado potato beetle and insects of the genus Diabrotica.

Still another aspect of the present invention relates to a biologically pure culture of a B.t. bacterium deposited with the Agricultural Research Culture Collection, Northern Regional Research Laboratory (NRRL) having Accession No. NRRL B-18655 and being designated as B.t. strain EG5144 and a biologically pure culture of a second bacterium deposited with the NRRL having Accession No. NRRL B-18920 and being designated as B.t. strain EG5145. B.t. strain EG5144 is a wild-type B.t. strain that carries the cryIIIC(b) gene (SEQ ID NO:1) and produces the insecticidal CryIIIC(b) protein (SEQ ID NO:2). B.t. strain EG5145 is also a wild-type B.t. strain, whose characteristics are similar to those of B.t. strain EG5144 described in more detail below. Biologically pure cultures of other B.t. bacteria carrying the cryIIIC(b) gene (SEQ ID NO:1) are also within the scope of this invention.

Yet another aspect of this invention relates to insecticidal compositions containing, in combination with an agriculturally acceptable carrier, either the CryIIIC(b) protein (SEQ ID NO:2) or fermentation cultures of a B.t. strain which has produced the CryIIIC(b) protein.

The invention also includes a method of controlling coleopteran insects by applying to a host plant for such insects an insecticidally effective amount of the CryIIIC(b) protein (SEQ ID NO:2) or of a fermentation culture of a B.t. strain that has made the CryIIIC(b) protein. The method is applicable to a variety of coleopteran insects, such as the Colorado potato beetle, Japanese beetle larvae (white grubs), Mexican bean beetle and corn rootworm.

Still another aspect of the present invention relates to a recombinant plasmid containing the cryIIIC(b) gene (SEQ ID NO:1), a biologically pure culture of a bacterium transformed with such recombinant plasmid, the bacterium preferably being B.t., such as B.t. strain EG7237 described in Example 6, as well as a plant transformed with the cryIIIC(b) gene.

BRIEF DESCRIPTION OF THE DRAWINGS

FIG. 1 comprises FIGS. 1A through 1C and shows the nucleotide base sequence of the cryIIIC(b) gene (SEQ ID NO:1) and the deduced amino acid sequence of the CryIIIC(b) protein (SEQ ID NO:2). The putative ribosome binding site (RBS) is indicated. Restriction sites for SspI and HindIII are also indicated.

FIG. 7 is a photograph of a Coomassie stained SDS-polyacrylamide gel. The gel shows protein bands synthesized by B.t. strain EG5144 (lane 1) and by recombinant B.t. strain EG7237 containing pEG272 (lane 3). Lane 2 contains a protein size standard and the numbers on either side of lanes 1 and 3 indicate approximate sizes, in kDa, of the crystal proteins produced by these strains.

DETAILED DESCRIPTION OF THE PREFERRED EMBODIMENTS

Figure 2:
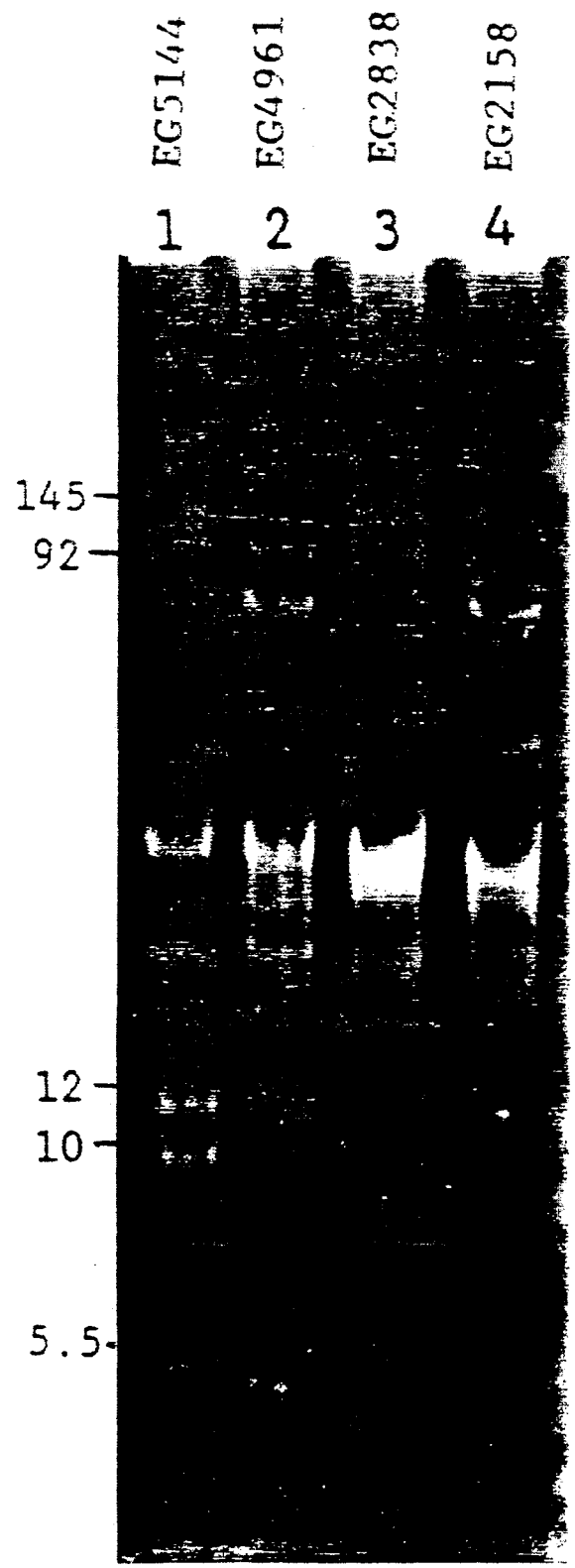
FIG. 2 is a photograph of an ethidium bromide stained agarose gel containing size fractionated native plasmids of B.t. strains EG5144 (lane 1), EG4961 (lane 2), EG2838 (lane 3) and EG2158 (lane 4). The numbers to the left of FIG. 2 indicate the approximate sizes, in megadaltons (MDa), of the plasmis of B.t. strain EG5144.

The isolation and purification of the cryIIIC(b) gene (SEQ ID NO:1) and the coleopteran-toxic CryIIIC(b) crystal protein (SEQ ID NO:2) and the characterization of the new B.t. strain EG5144 which produces the CryIIIC(b) protein are described at length in Examples 1-7. The utility of B.t. strain EG5144 and of the CryIIIC(b) crystal protein (SEQ ID NO:2) in insecticidal compositions and methods is also illustrated in Examples 8-11.

The cryIII-type gene of this invention, the cryIIIC(b) gene (SEQ ID NO:1), has the nucleotide base sequence shown in FIG. 1. The coding region of the cryIIIC(b) gene (SEQ ID NO:1) extends from nucleotide base position 14 to position 2099 shown in FIG. 1.

A comparison of the nucleotide base sequence of the cryIIIC[b]gene coding region with the corresponding coding region of the prior art cryIIIA gene indicates significant differences between the two genes. The cryIIIC(b) gene (SEQ ID NO:1) is only 76% homologous (positionally identical) with the cryIIIA gene.

A comparison of the nucleotide base sequence of the cryIIIC(b) gene coding region with the corresponding coding region of the cryIIIB gene obtained from recently discovered B.t. strain EG2838 (NRRL Accession No. B-18603) indicates that the cryIIIC(b) gene (SEQ ID NO:1) is 96% homologous (positionally identical) with the cryIIIB gene.

The CryIII-type protein of this invention, the CryIIIC(b) protein, that is encoded by the cryIIIC(b) gene (SEQ ID NO:1), has the amino acid sequence (SEQ ID NO:2) shown in FIG. 1. In this disclosure, references to the CryIIIC(b) "protein" are synonymous with its description as a "crystal protein", "protein toxin", "insecticidal protein" or the like, unless the context indicates otherwise. The size of the CryIIIC(b) protein (SEQ ID NO:2), as deduced from the DNA sequence of the cryIIIC(b) gene (SEQ ID NO:1), is 74,265 Daltons (Da).

The size of the CryIIIB protein, as deduced from the sequence of the cryIIIB gene, is 74,237 Da. The prior art CryIIIA protein, encoded by the cryIIIA gene, has a deduced size of 73,116 Da.

Despite the apparent size similarity, comparison of the amino acid sequence of the CryIIIC(b) protein (SEQ ID NO:2) with that of the prior art CryIIIA protein shows significant differences between the two. The CryIIIC(b) protein (SEQ ID NO:2) is only 68% homologous (positionally identical amino acids) with the CryIIIA protein. The CryIIIC(b) protein (SEQ ID NO:2) is 95% homolgous with the CryIIIB protein. Nevertheless, despite the apparent homology of the CryIIIC(b) and CryIIIB proteins, the CryIIIC(b) protein (SEQ ID NO:2) has been shown to be a different protein than the CryIIIB protein, based on its significantly improved insecticidal activity compared to the CryIIIB protein with respect to insects of the order Coleoptera and in particular, insects of the genus Diabrotica. The CryIIIC(b) protein (SEQ ID NO:2), unlike the CryIIIB protein, exhibits quantifiable insecticidal activity against corn rootworm larvae.

The present invention is intended to cover mutants and recombinant or genetically engineered derivatives, e.g., truncated versions, of the cryIIIC(b) gene (SEQ ID NO:1) that yield a protein with insecticidal properties essentially the same as those of the CryIIIC(b) protein (SEQ ID NO:2).

The cryIIIC(b) gene (SEQ ID NO:1) is also useful as a DNA hybridization probe, for discovering similar or closely related cryIII-type genes in other B.t. strains. The cryIIIC(b) gene (SEQ ID 0:1), or portions or derivatives thereof, can be labeled for use as a hybridization probe, e.g., with a radioactive label, using conventional procedures. The labeled DNA hybridization probe may then be used in the manner described in the Examples.

The cryIIIC(b) gene (SEQ ID NO:1) and the corresponding insecticidal CryIIIC(b) protein (SEQ ID NO:2) were first identified in B.t. strain EG5144, a novel B.t. isolate. The characteristics of B.t. strain EG5144 are more fully described in the Examples. Comparison of the plasmid arrays and other strain characteristics of B.t. strain EG5144 with those of the recently discovered B.t. strains EG2838 and EG4961 and those of the prior art B.t. strain EG2158 and B.t. var. tenebrionis (or the equivalent, B.t. var. san diego) demonstrates that each of these coleopteran-toxic B.t. strains is distinctly different. The plasmid array of B.t. strain EG5145, another wild-type strain isolated along with B.t. strain EG5144, is similar to that of B.t. strain EG5144, and B.t. strain EG5145 exhibits the same insecticidal activity against coleopteran insects, e.g., Japanese beetle larvae, as that of B.t. strain EG5144 (see Example 11).

The cryIIIC(b) gene (SEQ ID NO:1) may be introduced into a variety of microorganism hosts, using procedures well known to those skilled in the ar for transforming suitable hosts under conditions which allow for stable maintenance and expression of the cloned cryIIIC(b) gene. Suitable hosts that allow the cryIIIC(b) gene (SEQ ID NO:1) to be expressed and the CryIIIC(b) protein (SEQ ID NO:2) to be produced include *Bacillus thuringiensis* and other *Bacillus* species such as *B. subtilis* or *B. megaterium*. It should be evident that genetically altered or engineered microorganisms containing the cryIIIC(b) gene (SEQ ID NO:1) can also contain other toxin genes present in the same microorganism and that these genes could concurrently produce insecticidal crystal proteins different from the CryIIIC(b) protein.

The Bacillus strains described in this disclosure may be cultured using conventional growth media and standard fermentation techniques. The B.t. strains harboring the cryIIIC[b]gene (SEQ ID NO:1) may be fermented, as described in the Examples, until the cultured B.t. cells reach the stage of their growth cycle when CryIIIC(b) crystal protein (SEQ ID NO:2) is formed. For sporogenous B.t. strains, fermentation is typically continued through the sporulation stage when the CryIIIC(b) crystal protein is formed along with spores. The B.t. fermentation culture is then typically harvested by centrifugation, filtration or the like to separate fermentation culture solids, containing the CryIIIC(b) crystal protein, from the aqueous broth portion of the culture.

The B.t. strains exemplified in this disclosure are sporulating varieties (spore forming or sporogenous strains) but the cryIIIC(b) gene (SEQ ID NO:1) also has utility in asporogenous bacillus strains, i.e., strains that produced the crystal protein without production of spores. It should be understood that references to "fermentation cultures" of B.t. strains (containing the cryIIIC(b) gene (SEQ ID NO:1)) in this disclosure are intended to cover sporulated B.t. cultures, i.e., B.t. cultures containing the CryIIIC(b) crystal protein and spores, and sporogenous Bacillus strains that have produced crystal protein during the vegetative stage, as well as asporogenous Bacillus strains containing the cryIIIC(b) gene (SEQ ID NO:1) in which the culture has reached the growth stage where crystal protein is actually produced.

The separated fermentation solids are primarily CryIIIC(b) crystal protein (SEQ ID NO:2) and B.t. spores, along with some cell debris, some intact cells, and residual fermentation medium solids. If desired, the crystal protein may be separated from the other recovered solids via conventional methods, e.g., sucrose density gradient fractionation. Highly purified CryIIIC(b) protein (SEQ ID NO:2) may be obtained by solubilizing the recovered crystal protein and then precipitating the protein from solution.

The CryIIIC(b) protein (SEQ ID NO:2), as noted earlier, is a potent insecticidal compound against coleopteran insects, such as the Colorado potato beetle, Japanese beetle larvae (white grubs), Mexican bean beetle and the like. The CryIIIC(b) protein (SEQ ID NO:2), in contrast to the CryIIIA and CryIIIB proteins, exhibits measurable insecticidal activity against Diabrotica insects, e.g., corn rootworms, which have been relatively unaffected by other coleopteran-toxic B.t. crystal proteins. The CryIIIC(b) protein (SEQ ID NO:2) may be utilized as the active ingredient in insecticidal formulations useful for the control of coleopteran insects such as those mentioned above. Such insecticidal formulations or compositions typically contain agriculturally acceptable carriers or adjuvants in addition to the active ingredient and are prepared and used in a manner well known to those skilled in the art.

The CryIIIC(b) protein (SEQ ID NO:2) may be employed in insecticidal formulations in isolated or purified form, e.g., as the crystal protein itself. Alternatively, the CryIIIC(b) protein (SEQ ID NO:2) may be present in the recovered fermentation solids, obtained from culturing of a Bacillus strain, e.g., *Bacillus thuringiensis,* or other microorganism host carrying the cryIIIC(b) gene (SEQ ID NO:1) and capable of producing the CryIIIC(b) protein. Preferred Bacillus hosts include B.t. strain EG5144 and genetically improved B.t. strains derived from B.t. strain EG5144. The latter B.t. strains may be obtained via plasmid curing and/or conjugation techniques and contain the native cryIIIC(b) gene-containing plasmid from B.t. strain EG5144. Genetically engineered or transformed B.t. strains or other host microorganisms containing a recombinant plasmid that expresses the cloned cryIIIC(b) gene (SEQ ID NO:1), obtained by recombinant DNA procedures, may also be used.

An example of such transformants is B.t. strain EG7237, which contains the cloned cryIIIC(b) gene (SEQ ID NO:1) on a recombinant plasmid.

The recovered fermentation solids contain primarily the crystal protein and (if a sporulating B.t. host is employed) spores; cell debris and residual fermentation medium solids may also be present. The recovered fermentation solids containing the CryIIIC(b) protein may be dried, if desired, prior to incorporation in the insecticidal formulation.

The formulations or compositions of this invention containing the insecticidal CryIIIC(b) protein (SEQ ID NO:2) as the active component are applied at an insecticidally effective amount which will vary depending on such factors as, for example, the specific coleopteran insects to be controlled, the specific plant or crop to be treated and the method of applying the insecticidally active compositions. An insecticidally effective amount of the insecticide formulation is employed in the insect control method of this invention.

The insecticide compositions are made by formulating the insecticidally active component with the desired agriculturally acceptable carrier. The formulated compositions may be in the form of a dust or granular material, or a suspension in oil (vegetable or mineral) or water or oil/water emulsions, or as a wettable powder, or in combination with any other carrier material suitable for agricultural application. Suitable agricultural carriers can be solid or liquid and are well known in the art. The term "agriculturally acceptable carrier" covers all adjuvants, e.g., inert components, dispersants, surfactants, tackifiers, binders, etc. that are ordinarily used in insecticide formulation technology; these are well known to those skilled in insecticide formulation.

The formulations containing the CryIIIC(b) protein (SEQ ID NO:2) and one or more solid or liquid adjuvants are prepared in known manners, e.g., by homogeneously mixing, blending and/or grinding the insecticidally active CryIIIC(b) protein component with suitable adjuvants using conventional formulation techniques.

The insecticidal compositions of this invention are applied to the environment of the target coleopteran insect, typically onto the foliage of the plant or crop to be protected, by conventional methods, preferably by spraying. Other application techniques, e.g., dusting, sprinkling, soaking, soil injection, seed coating, seedling coating or spraying, or the like, are also feasible and may be required for insects that cause root or stalk infestation. These application procedures are well known in the art.

The cryIIIC(b) gene (SEQ ID NO:1) or its functional equivalent, hereinafter sometimes referred to as the "toxin gene," can be introduced into a wide variety of microorganism hosts. Expression of the cryIIIC(b) gene (SEQ ID N :1) results in the production of insecticidal CryIIIC(b) crystal protein toxin (SEQ ID NO:2). Suitable hosts include B.t. and other species of Bacillus, such as B. subtilis or B. megaterium, for example. Plant-colonizing or root-colonizing microorganisms may also be employed as the host for the cryIIIC(b) gene (SEQ ID NO:1). Various procedures well known to those skilled in the art are available for introducing the cryIIIC(b) gene (SEQ ID NO:1) into the microorganism host under conditions which allow for stable maintenance and expression of the gene in the resulting transformants.

The transformants, i.e., host microorganisms that harbor a cloned gene in a recombinant plasmid, can be isolated in accordance with conventional methods, usually employing a selection technique, which allows growth of only those host microorganisms that contain a recombinant plasmid. The transformants then can be tested for insecticidal activity. Again, these techniques are standard procedures.

Characteristics of particular interest in selecting a host cell for purposes of production include ease of introducing the gene into the host, availability of expression systems, efficiency of expression, stability of the CryIIIC(b) insecticidal protein in the host, and the presence of auxiliary genetic capabilities. The cellular host containing the insecticidal cryIIIC(b) gene (SEQ ID NO:1) may be grown in any convenient nutrient medium, where expression of the cryIIIC(b) gene is obtained and CryIIIC(b) protein (SEQ ID NO:2) produced, typically to sporulation. The sporulated cells containing the crystal protein may then be harvested in accordance with conventional methods, e.g., centrifugation or filtration.

The cryIIIC(b) gene (SEQ ID NO:1) may also be incorporated into a plant which is capable of expressing the gene and producing CryIIIC(b) protein (SEQ ID NO:2), rendering the plant more resistant to insect attack. Genetic engineering of plants with the cryIIIC(b) gene (SEQ ID NO:1) may be accomplished by introducing the desired DNA containing the gene into plant tissues or cells, using DNA molecules of a variety of forms and origins that are well known to those skilled in plant genetic engineering. An example of a technique for introducing DNA into plant tissue is disclosed in European Patent Application Publication No. 0 289 479, published Nov. 2, 1988, of Monsanto Company.

DNA containing the cryIIIC(b) gene (SEQ ID NO:1) or a modified cryIIIC(b) gene capable of producing the CryIIIC(b) protein (SEQ ID NO:2) may be delivered into the plant cells or tissues directly by infectious plasmids, such as Ti, the plasmid from *Agrobacterium tumefaciens*, viruses or microorganisms like *A. tumefaciens*, by the use of lysosomes or liposomes, by microinjection by mechanical methods and by other techniques familiar to those skilled in plant genetic engineering.

Variations may be made in the cryIIIC(b) gene nucleotide base sequence (SEQ ID NO:1), since the various amino acids forming the protein encoded by the gene usually may be determined by more than one codon, as is well known to those skilled in the art. Moreover, there may be some variations or truncation in the coding regions of the cryIIIC(b) nucleotide base sequence which allow expression of the gene and production of functionally equivalent forms of the CryIIIC(b) insecticidal protein. These variations which can be determined without undue experimentation by those of ordinary skill in the art with reference to the present specification are to be considered within the scope of the appended claims, since they are fully equivalent to the specifically claimed subject matter.

The present invention will now be described in more detail with reference to the following specific, nonlimiting examples. The examples relate to work which was actually done based on techniques generally known in the art and using commercially available equipment.

The novel B.t. strain EG5144 was isolated following the procedure described in Example 1. The procedures described in Example 1 were also used to isolate the novel B.t. strain EG5145.

EXAMPLE 1

Isolation of B.t. Strains EG5144 and EG5145

Crop dust samples were obtained from various sources throughout the U.S. and abroad, typically grain storage facilities. The crop dust samples were treated by suspending the crop dust in an aqueous buffer and heating the suspension at 60° C. for 30 min. to enrich for heat resistant spore forming Bacillus-type bacteria such as B.t. The treated dust suspensions were diluted in aqueous buffer, and the dilutions were spread on agar plates to allow each individual bacterium from the crop dust to grow into a colony on the surface of the agar plate. After growth, a portion of each colony was transferred from the agar plate to a nitrocellulose filter. The filter was treated with NaOH to lyse the colonies and to fix the DNA from each colony onto the filter.

A modified treatment procedure was developed for use with B.t. colonies utilized in the colony hybridization procedure, since standard techniques applicable to E.coli were found to be unworkable with B.t. In the treatment described above, special conditions were required to assure that the B.t. colonies were in a vegetative state of growth, making them susceptible to lysis with NaOH. Accordingly, after a portion of each colony was transferred to the nitrocellulose filter, the filter was placed colony side up on an agar medium containing 0.5% (w/v) glucose. The transferred colonies were then allowed to grow on the agar-glucose medium for 5 hours at 30° C. Use of 0.5% glucose in the agar medium and the 5-hour, 30° C. growth cycle were critical for assuring that the B.t. colonies were in a vegetative state and thus susceptible to lysis.

A cloned coleopteran toxin gene was used as a specific probe to find other novel and rare coleopteran-toxic strains of B.t. from crop dust samples. A 2.9 kb HindIII DNA restriction fragment containing the cryIIIA gene, formerly known as the cryC gene of B.t. strain EG2158, described in Donovan et al., Mol.Gen.-Genet., 214, pp.365–372 (1988), was used as a probe in colony hybridization procedures.

The 2.9 kb HindIII cryIIIA DNA fragment, containing the entire cryIIIA gene, was radioactively labeled with [alpha-P$^{32}$]-dATP and Klenow enzyme, by standard methods. The nitrocellulose filters containing the DNA from each lysed colony were incubated at 65° C. for 16 hours in a buffered solution that contained the radioactively labeled 2.9 kb HindIII cryIIIA DNA probe to hybridize the DNA from the colonies with the DNA from the radioactively labeled cryIIIA probe. The 65° C. hybridization temperature was used to assure that the cryIIIA DNA probe would hybridize only to DNA from colonies that contained a gene that was similar to the cryIIIA DNA probe.

The 2.9 kb cryIIIA probe hybridized to many B.t. colonies from various samples of crop dust. Examination of these colonies revealed, unexpectedly, that they did not contain any cryIII-type genes. These colonies did contain cryI-type genes. The cryI-type genes encode lepidopteran-toxic, coleopteran-nontoxic crystal proteins with molecular masses of approximately 130 kDa. Computer-assisted comparisons of the sequence of the cryIIIA gene with the sequence of several cryI-type genes revealed that the 3'-end of the cryIIIA gene was partially homologous with portion of the cryI-type genes. This finding supported the belief that the 3'-end of the cryIIIA gene was causing the 2.9 kb cryIIIA probe to hybridize to B.t. colonies containing cryI-type genes.

To correct this problem, the 2.9 kb HindIII cryIIIA probe was digested with the enzyme XbaI and a 2.0 kb HindIII-XbaI fragment was purified that contained the cryIIIA gene minus its 3'-end. The 2.0 kb HindIII-XbaI fragment contains the 3'-truncated cryIIIA gene. When the 2.0 kb fragment was used in repeated colony hybridization experiments, it did not hybridize to cryI gene-containing B.t. colonies.

Approximately 48,000 Bacillus-type colonies from crop dust samples from various locations were probed with the radioactively labeled 2.0 kb HindIII-XbaI cryIIIA probe. Only one novel B.t. strain from an Illinois crop dust sample was discovered that specifically hybridized to the cryIIIA probe. That novel strain was designated B.t. strain EG2838, which has been deposited with the NRRL unde Accession No. NRRL B-18603.

Subsequently, approximately 50,000 additional Bacillus-type colonies from crop dust samples were also screened with the radioactively labeled 2.0 kb HindIII-XbaI cryIIIA probe, but without success in identifying any other strains containing novel cryIII-type genes.

B.t. strain EG2838 was found to be insecticidally active against coleopteran insects, notably, the Colorado potato beetle. B.t. strain EG2838 did not have substantial insecticidal activity with respect to the southern corn rootworm. A gene, designated the cryIIIB gene, was isolated from B.t. strain EG2838, and its nucleotide base sequence determined. The cryIIIB gene encoded a crystal protein, designated the CryIIIB protein, containing 651 amino acids having a deduced size of 74,237 Daltons. The size of the prior art CryIIIA protein had previously been deduced to be 73,116 Daltons (644 amino acids). The cryIIIB gene is 75% homologous with the cryIIIA gene, and the CryIIIB protein is 68% homologous with the CryIIIA protein.

Thousands of Bacillus-type colonies from numerous crop dust samples from various locations from around the world were screened with a cryIIIB probe obtained from B.t. strain EG2838. The cryIIIB probe was radioactively labeled using the procedure set forth above with respect to the radioactively labeled cryIIIA probe. The radioactively labeled cryIIIB probe consisted of a 2.4 kb SspI restriction fragment of DNA from B.t. strain EG2838. The fragment contains the complete protein coding region for the coleopteran toxin cryIIIB gene of B.t. strain EG2838. Ultimately, the B.t. strains of the present invention, designated B.t. strains EG5144 and EG5145, were isolated from a crop dust sample via B.t. colonies that specifically hybridized to the cryIIIB probe.

To characterize B.t. strain EG5144, several studies were conducted. One series of studies was performed to characterize its flagellar serotype. Additional studies were conducted to determine the sizes of the native plasmids in B.t. strain EG5144 and to ascertain which plasmids contained genes that encoded coleopteran-active insecticidal crystal proteins. DNA blot analysis was thereafter performed using size fractionated total DNA restriction fragments from B.t. strain EG5144, compared with similarly-processed total DNA from other B.t. strains containing cryIII-type toxin genes, to demonstrate that B.t. strain EG5144 contains a unique coleopteran-active toxin gene. In addition, B.t. strain EG5144 was evaluated further by characterizing the crystal proteins it produces and by measuring the insecticidal activity associated with B.t. strain EG5144 and its crystal proteins. Examples 2 through 7 are directed to the procedures for characterizing B.t. strain EG5144 and its unique cryIII-type gene, and Examples 8 through 11 are directed to the insecticidal activity of B.t. strain EG5144 and of B.t. strain EG7237, containing the cryIIIC(b) gene (SEQ ID NO:1) of this invention.

EXAMPLE 2

Evaluation of the Flagellar Serotype of B.t. Strain EG5144

Flagellar serotyping studies were carried out with B.t. strain EG5144, using an antibody mediated cell agglutinization assay (Craigie et al., *J.Immunol.*, 21, pp.417–511 (1936)). Flagellar antibody reagents were prepared using purified flagella from B.t. var. kurstaki, morrisoni an tolworthi type-strains and from the novel coleopteran-active B.t. strain EG4961.

The study included formalin-fixed vegetative cells of B.t. strain EG5144 and of cells of other coleopteran-active B.t. strains and of several common B.t. type-strains, each of which were scored for flagellar antibody mediated cell agglutinization.

The other coleopteran-active B.t. strains included B.t. var. *tenebrionis*, B.t. var. *san diego*, B.t. strain EG2158 (all containing the cryIIIA gene); B.t. strain EG2838 (containing the cryIIIB gene); and B.t. strain EG4961 (containing a novel coleopteran toxin-encoding gene designated as the cryIIIC(a) gene).

The B.t. flagellar type-strains were B.t. var. kurstaki (HD-1, serotype 3ab), B.t. var. morrisoni (HD-12, serotype 8ab) and B.t. var. tolworthi (HD-13, serotype 9).

Results of this study are shown in Table 1; "+" indicates that a cross-reaction occurred and "−" indicates that no cross-reaction occurred.

TABLE 1

| Cells | Flagellar Antibody Reagent | | | |
|---|---|---|---|---|
| | kurstaki | morrisoni | tolworthi | EG4961 |
| B.t. strain EG5144 | − | − | − | − |
| B.t. var. tenebrionis | − | + | − | − |
| B.t. var. san diego | − | + | − | − |
| B.t. strain EG2158 | − | + | − | − |
| B.t. strain EG2838 | − | − | + | − |
| B.t. strain EG4961 | − | − | − | + |
| Other B.t. flagellar type-strains: | | | | |
| B.t. var. kurstaki (HD-1) | + | − | − | − |
| B.t. var. morrisoni (HD-12) | − | + | − | − |
| B.t. var. tolworthi (HD-13) | − | − | + | − |

The results in Table 1 show that cells of B.t. strain EG5144 gave a negative reaction with B.t. type-strain kurstaki, morrisoni and tolworthi flagella antibody reagents. B.t. strain EG5144 cells also gave a negative reaction with flagellar reagent from B.t. strain EG4961, a novel coleopteran-active strain that has been discovered to exhibit Diabrotica toxicity.

These results indicate that B.t. strain EG5144 is not a kurstaki, morrisoni or tolworthi-type B.t. strain. Furthermore, the flagellar serotype of B.t. strain EG5144, which is yet not known, is apparently different from that of B.t. strain EG4961, which has been serotyped as serovar kumamotoensis (serotype 18). Both B.t. strain EG5144 and B.t. strain EG4961 appear to have flagellar serotypes that are different from those of other coleopteran-toxic B.t. strains reported in the literature.

EXAMPLE 3

Size Fractionation and cryIIIB Probing of Native Plasmids of EG5144

B.t. strains may be characterized by fractionating their plasmids according to size by the well-known procedure of agarose gel electrophoresis. This procedure involves lysing B.t. cells with lysozyme and SDS, electrophoresing plasmids from the lysate through an agarose gel and staining the gel with ethidium bromide to visualize the plasmids. Larger plasmids, which move more slowly through the gel, appear at the top of the gel and smaller plasmids appear toward the bottom of the gel.

The agarose gel in FIG. 2 shows that B.t. strain EG5144 contains native plasmids of approximately 145, 92, 12, 10 and 5.5 MDa, as indicated by the white horizontal bands. Plasmid sizes were estimated by comparison to plasmids of known sizes (not shown). Although not shown on FIG. 2, B.t. strain EG5145 contains native plasmids of approximately 145, 92, 12 and 5.5 MDa. The cryptic 10 MDa plasmid found in B.t. strain EG5144 is not present in B.t. strain EG5145.

FIG. 2 further shows that the ooleopteran-toxic B.t. strain EG4961 contains native plasmids of about 150, 95, 70, 50, 5 and 1.5 MDa and that the coleopteran-toxic B.t. strain EG2838 contains native plasmids of about 100, 90 and 37 MDa. FIG. 2 also shows that the eoleopteran-toxic B.t. strain EG2158 contains native plasmids of about 150, 105, 88, 72, and 35 MDa. Some of the plasmids, such as the 150 and 1.5 MDa plasmids of B.t. strain EG4961 and the 150 MDa plasmid of B.t. strain EG215s, may not be visible in the photograph, although they are visible in the actual gel. FIG. 2 demonstrates that the sizes of the native plasmids of B.t. strain EG5144 are different from the sizes of the native plasmids of B.t. strains EG2158, EG2838 and EG4961. B.t. strain EG5144 is therefore distinct from the other coleopteran-toxic B.t. strains EG2158, EG2838 and EG4961, based on these plasmid array studies and on the serotyping studies described in Example 2. Likewise, B.t. strain EG5145 appears distinct from the coleopteran-toxic B.t. strains noted above based on plasmid array studies.

The plasmids shown in FIG. 2 were transferred by blotting from the agarose gel to a nitrocellulose filter using the blot techniques of Southern, J.Molec.Biol., 98, pp.503–517 (1975), and the filter was hybridized as described above with the radioactively labeled 2.4 kb cryIIIB DNA probe. After hybridization, the filter was exposed to X-ray film. Examination of the X-ray film confirmed that the cryIIIB probe specifically hybridized to the 92 MDa plasmid of B.t. strain EG5144. This result demonstrates that the 92 MDa plasmid of B.t. strain EG5144 contains a DNA sequence that is at least partly homologous to the cryIIIB gene and confirms that the 92 MDa plasmid contains a cryIII-type gene. The X-ray film also showed that the cryIIIB probe hybridized, as expected, to the 95 MDa plasmid of B.t. strain EG4961 and to the 100 MDa plasmid of B.t. strain EG2838, and to the 88 MDa plasmid of B.t. strain EG2158. The 88 MDa plasmid of B.t. strain EG2158 has been previously shown to contain the coleopteran-toxin cryIIIA gene (see Donovan et al., *Mol.Gen.Genet.*, 214, pp.365–372 (1988)). The inventors have previously determined that the 100 MDa plasmid of B.t. strain EG2838 contains the coleopteran toxin cryIIIB gene and that the 95 MDa plasmid of B.t. strain EG4961 contains the novel coleopteran toxin cryIIIC(a) gene.

EXAMPLE 4

Blot Analysis of DNA from B.t. strains EG5144 and EG5145

Both chromosomal and plasmid DNA (total DNA) from B.t. strain EG5144 were extracted and digested with separate restriction enzymes, SspI, HindIII and EcoRI. The digested DNA was size fractionated by electrophoresis through an agarose gel, and the fragments were then visualized by staining with ethidium bromide. For comparison, total DNA from the coleopteran-toxic B.t. strains EG2158, EG2838 and EG4961 was processed in an identical manner. Examination of the resultant stained agarose gel showed that restriction digestions of total DNA from these B.t. strains with each of SspI, HindIII and EcoRI yield hundreds of DNA fragments of various sizes.

Figure 3:
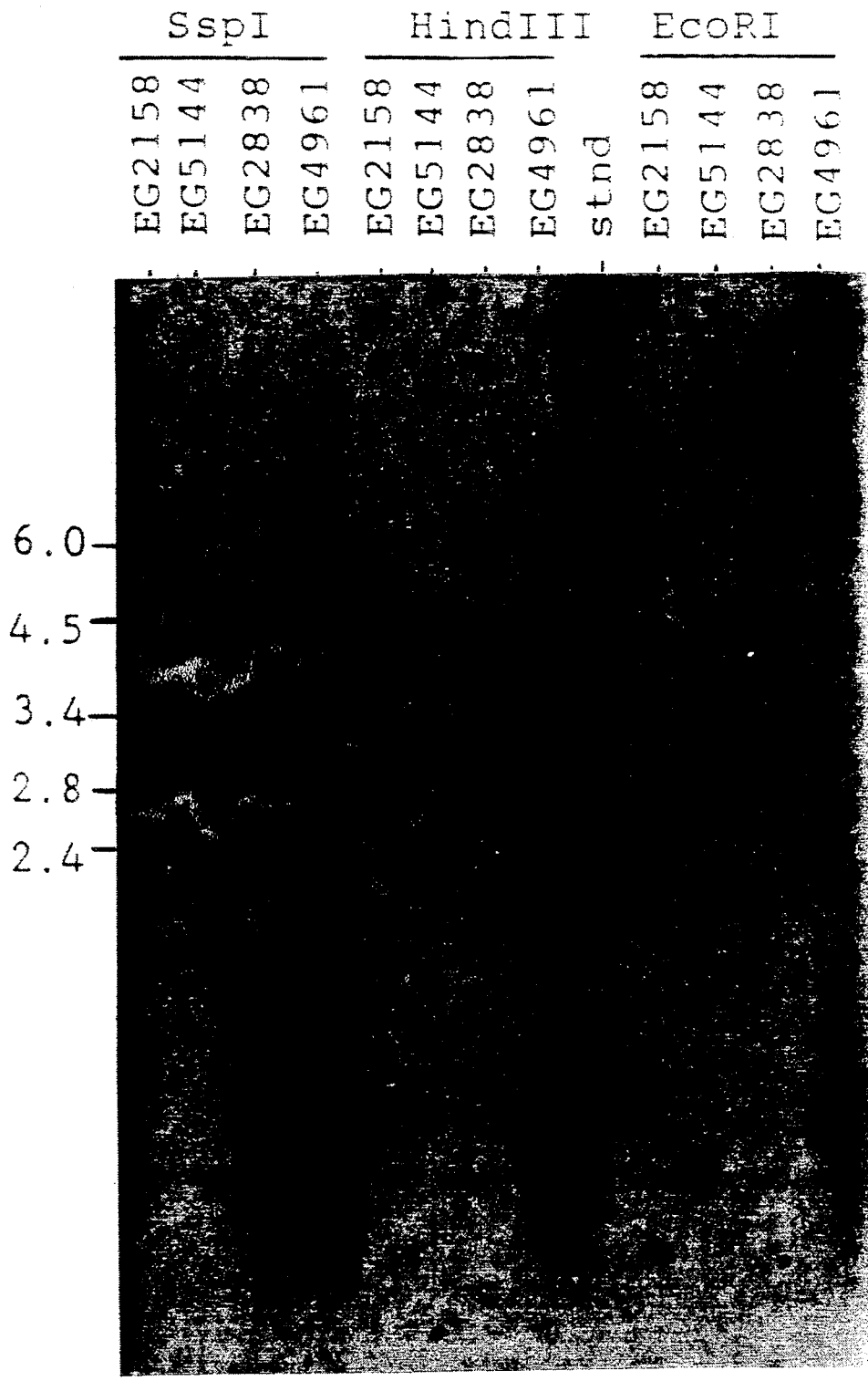
FIG. 3 is a photograph of an autoradiogram made by transferring size fractionated DNA fragments from an agarose gel to a nitrocellulose filter, hybridizing the filter with a radioactively labeled 2.4 kilobases (kb) cryIIIB probe, and exposing the filter to X-ray film. The agarose gel contained size fractionated total DNA fragments from B.t. strains EG2158, EG5144, EG2838 and EG4961, that had been obtained in separate digestions with the restriction enzymes SspI, HindIII and EcoRI. The numbers to the left of FIG. 3 indicate the sizes, in kb, of B.t. strain EG514 restriction fragments that hybridized to the cryIIIB probe. The lane labeled "stnd" is a size standard.

The size fractionated DNA restriction fragments were transferred by blotting from the agarose gel to a nitrocellulose filter and were then probed with a cryIII-type DNA hybridization probe. The filter was hybridized at 65° C. in a buffered aqueous solution containing a radioactively labeled 2.4 kb cryIIIB DNA probe. After hybridization, the filter was exposed to X-ray film to make an autoradiogram. FIG. 3 is a photograph of the autoradiogram where the numbers to the left indicate the size, in kb, of the DNA fragments of B.t. strain EG5144 that hybridized to the cryIIIB probe. These sizes were determined by comparison with the lane labeled "stnd" which contained phage lambda DNA digested with HindIII and radioactively labelled as size markers. Lanes in FIG. 3 marked EG2158, EG5144, EG2838 and EG4961 contain size fractionated DNA fragments from these respective B.t. strains, obtained by digestion with the restriction enzyme designated above the individual lanes.

In the lanes for each B.t strain in FIG. 3, the dark bands represent DNA restriction fragments that hybridized with the cryIIIB probe. Visual inspection of FIG. 3 shows that the sizes of the cryIIIB-hybridizing restriction fragments of B.t. strain EG5144 are distinctly different from the sizes of the cryIIIB-hybridizing fragments of B.t. strains EG2158, EG2838 and EG4961.

In particular, the size of the cryIIIB-hybridizing SspI restriction fragment for B.t. strain EG5144 is 3.4 kb, and this is unlike the corresponding SspI restriction fragments for the other three B.t. strains: 2.8 kb for B.t. strain EG2158; 2.4 kb for B.t. strain EG2838; and 4.5 and 6.0 kb for B.t. strain EG4961. Similar differences are apparent for the DNA restriction fragments obtained using HindIII and EcoRI.

These restriction pattern results suggest that B.t. strain EG5144 contains a cryIII-type gene that is different from the cryIIIA, cryIIIB and cryIIIC(a) genes of B.t. strains EG2158, EG2838 and EG4961, respectively. The cryIII-type gene of B.t. strain EG5144 has been designated cryIIIC(b) (SEQ ID NO:1) by the inventors.

Total DNA from B.t. strain EG5144 and B.t. strain EG5145 was extracted and digested with six separate restriction enzymes (HindIII, EcoRI, AccI, DraI, SspI, XbaI), and size fractionated by electrophoresis on an agarose gel. The size fractionated DNA restriction fragments were then transferred by blotting to a nitrocellulose filter and were then probed with a cryIII-type DNA hybridization probe, specifically a probe containing cryIIIA. After hybridization, the filter was exposed to X-ray film to make an autoradiogram. The restriction pattern results were identical for the two B.t. strains evaluated, EG5144 and EG5145, which suggests that the two strains contain the same cryIII-type gene.

EXAMPLE 5

Characterization of Crystal Proteins of B.t. Strain EG5144

B.t. strain EG5144 was grown in DSMG sporulation medium at room temperature (about 21°-25° C.) until sporulation and cell lysis had occurred (4 to 5 days growth). The DSMG medium is 0.4% (w/v) Difco nutrient broth, 25 mM $K_2HPO_4$, 25 mM $KH_2PO_4$, 0.5 mM $Ca(NO_3)_2$, 0.5 mM $MgSO_4$, 10 μM $FeSO_4$, 10 μM $MnCl_2$ and 0.5% (w/v) glucose. The sporulated culture of B.t. strain EG5144 was observed microscopically to contain free floating, irregularly shaped crystals in addition to B.t. spores. Experience has shown that B.t. crystals are usually composed of proteins that may be toxic to specific insects. The appearance of the crystals of B.t. strain EG5144 differed from the flat, rectangular (or rhomboidal) crystals of B.t. strain EG2158, but partially resembled some of the irregularly shaped crystals of B.t. strains EG2838 and EG4961.

Spores, crystals and residual lysed cell debris from the sporulated culture of B.t. strain EG5144 were harvested by centrifugation. The recovered solids were washed once with aqueous 1N NaCl and twice with TETX (containing 10 mM Tris HCl pH 7.5, 1 mM EDTA and 0.005% (w/v) Triton ® X-100) and suspended in TETX at a concentration of 50 mg/ml. The washed crystals were specifically solubilized from 250μg centrifuged fermentation culture solids (containing crystals, spores and some cell debris) by heating the solids mixture in a solubilization buffer (0.14 M Tris pH 6.8, 2% (w/v) SDS, 5% (v/v) 2-mercaptoethanol, 10% (v/v) glycerol and 0.1% (v/v) bromophenol blue) at 100° C. for 5 minutes. The solubilized crystal proteins were size fractionated by SDS-PAGE. After size fractionation, the proteins were visualized by staining with Coomassie dye. Cultures of B.t. strains EG4961, EG2158 and EG2838 were processed in an identical manner for purposes of comparison.

Figure 4:
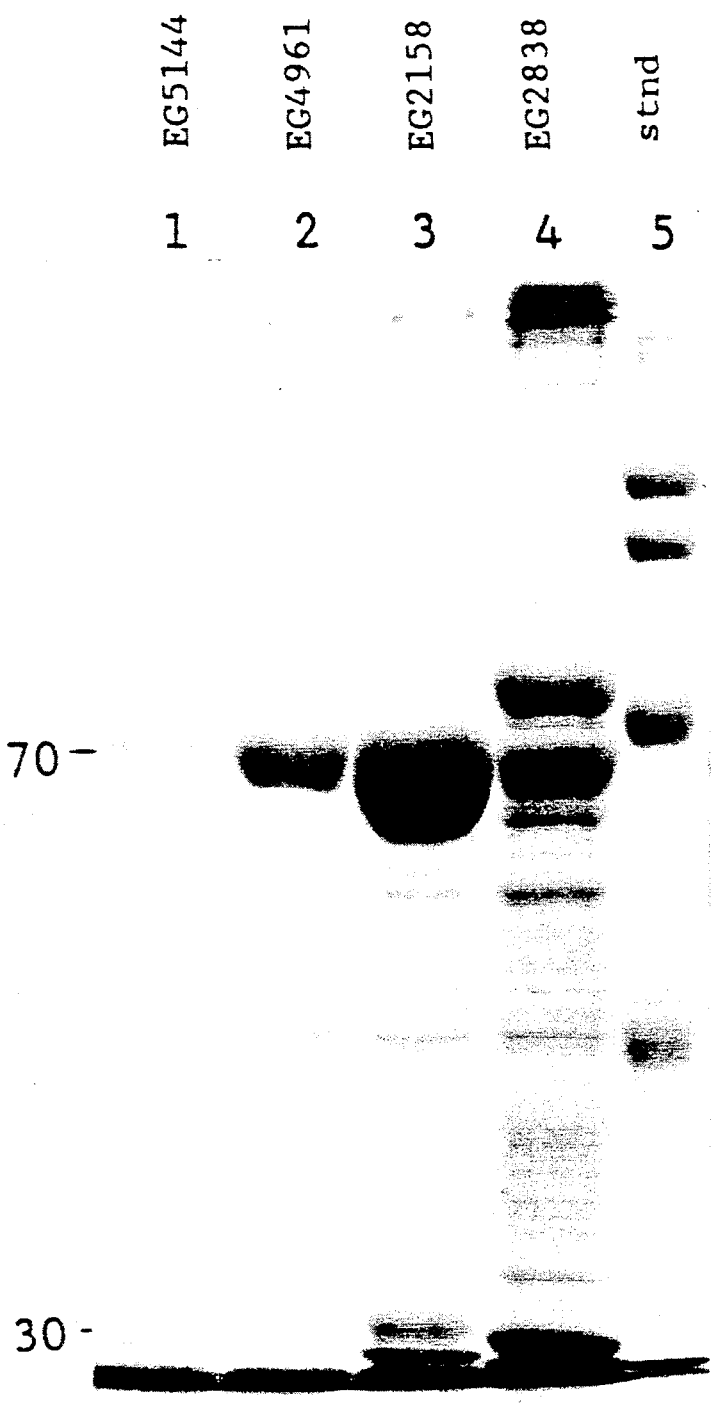
FIG. 4 is a photograph of a Coomassie stained sodium dodecyl sulfate ("SDS") polyacrylamide gel showing crystal proteins solubilized from B.t. strains EG5144 (lane 1), EG4961 (lane 2), EG2158 (lane 3) and EG2838 (lane 4). The numbers to the left of FIG. 4 indicate the approximate sizes in kDa of the crystal proteins produced by B.t. strain EG5144. Lane 5 contains protein molecular size standards.

FIG. 4 shows the results of this protein size fractionation analysis where the numbers to the left indicate the size, in kDa, of the crystal proteins synthesized by B.t. strain EG5144. As shown in lane 1, a major protein of approximately 70 kDa and a minor protein of approximately 30 kDa were solubilized from centrifuged fermentation solids containing B.t. strain EG5144 spores and crystals. The approximately 70 kDa protein of B.t. strain EG5144 appears similar in size to the approximately 70 kDa coleopteran-toxic crystal proteins of B.t. strains EG4961 (lane 2), EG2158 (lane 3) and to the approximately 74 kDa coleopteran-toxic crystal protein of B.t. strain EG2838 (lane 4).

Previous work by the inventors has shown that the coleopteran-toxic crystal proteins of B.t. strains EG4961, EG2158 and EG2838 are each different. The CryIIIC(a) protein of B.t. strain EG4961 is coded by the cryIIIC(a) gene and has a deduced size of 74,393 Da. The CryIIIA protein of B.t. strain EG2158 is coded by the cryIIIA gene and has a deduced size of 73,116 Da. The CryIIIB protein of B.t. strain EG2838 is coded by the cryIIIB gene and has a deduced size of 74,237 Da. As described in Example 6, the coleopteran-toxic crystal protein of B.t. strain EG5144 produced by the novel cryIIIC(b) gene (SEQ ID NO:1) is clearly different from the CryIIIA, CryIIIB and CryIIIC(a) proteins.

The minor crystal protein of approximately 30 kDa that is produced by B.t. strain EG5144 is roughly similar in size to small crystal proteins produced by B.t. strains EG4961, EG2158 and EG2838. The approximately 30 kDa minor proteins of B.t. strains EG2158, EG2838 and EG4961 appear to be related to each other and none has been found to exhibit measurable insecticidal activity towards coleopteran insects. There is no reason to believe that the approximately 30 kDa protein of B.t. strain EG5144 possesses insecticidal activity against coleopteran insects.

Following the procedure of Example 4, further DNA blot analysis revealed that the 2.4 kb cryIIIB DNA probe specifically hybridized to a single 7.0 kb EcoRI-XbaI restriction fragment of B.t. strain EG5144 DNA. This result suggested that the 7.0 kb fragment contained the complete cryIIIC(b) gene.

The 7.0 kb EcoRI-XbaI fragment of B.t. strain EG5144 was isolated and studies were conducted on the 7.0 kb EcoRI-XbaI restriction fragment to confirm that the fragment contained a cryIII-type gene, in particular, the cryIIIC(b) gene. The procedures set forth in Example 6 describe the determination of the nucleotide base sequence of the cryIIIC(b) gene (SEQ ID NO:1).

EXAMPLE 6

Cloning and Sequencing of the cryIIIC(b) Gene of B.t. Strain EG5144

In order to isolate the 7.0 kb EcoRI-XbaI fragment described in the previous Example, a plasmid library of B.t. strain EG5144 was constructed by ligating size-selected DNA EcoRI-XbaI restriction fragments from B.t. strain EG5144 into the well-known E.coli vector pUC18. This procedure involved first obtaining total DNA from B.t. strain EG5144 by cell lysis followed by DNA spooling, then double digesting the total DNA with both EcoRI and XbaI restriction enzymes, electrophoresing the digested DNA through an agarose gel, excising a gel slice containing 4–10 kb size selected fragments of DNA, and electroeluting the size selected EcoRI-XbaI restriction fragments from the agarose gel slice. These fragments were mixed with the E.coli plasmid vector pUC18, which had also been digested with EcoRI and XbaI. The pUC18 vector carries the gene for ampicillin resistance (Amp$^r$) and the vector replicates in E.coli. T4 DNA ligase and ATP were added to the mixture of size-selected restriction fragments of DNA from B.t strain EG5144 and of digested pUC18 vector to allow the pUC18 vector to ligate with the B.t. strain EG5144 restriction fragments.

The plasmid library was then transformed into E. coli cells, a host organism lacking the gene of interest, as follows. After ligation, the DNA mixture was incubated with an ampicillin sensitive E. coli host strain, E. coli strain DH5α, that had been treated with CaCl$_2$ to allow the cells to take up the DNA. E. coli, specifically strain DH5α, was used as the host strain because these cells are easily transformed with recombinant plasmids and because E. coli strain DH5α does not naturally contain genes for B.t. crystal proteins. Since pUC18 confers resistance to ampicillin, all host cells acquiring a recombinant plasmid would become ampicillin resistant. After exposure to the recombinant plasmids, the E. coli host cells were spread on agar medium that contained ampicillin. After incubation overnight at a temperature of 37° C., several thousand E. coli colonies grew on the ampicillin-containing agar from those cells which harbored a recombinant plasmid. These E. coli colonies were then blotted onto nitrocellulose filters for subsequent probing.

Figure 5:
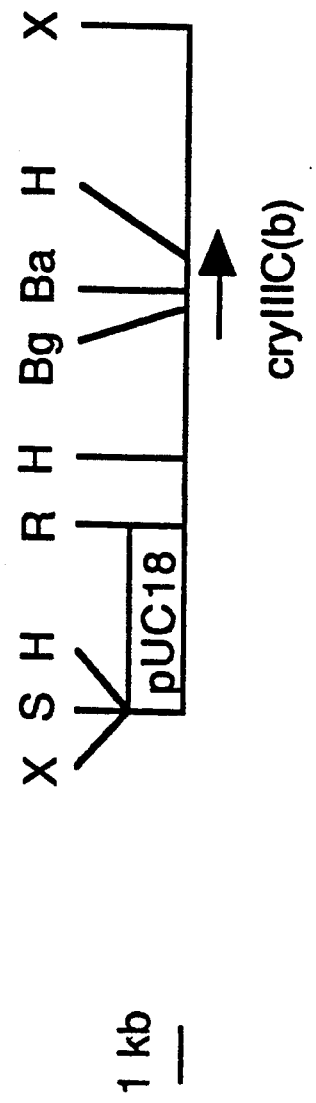
FIG. 5 shows a restriction map of plasmid pEG271. The location and orientation of the cryIIIC(b) gene (SEQ ID NO:1) is indicated by the arrow. Plasmid pEG271 is functional in *Escherichia coli* (E.coli), since it contains *E. coli* plasmid pUC18 (Ap$^r$), indicated by the segment marked pUC18. The abbreviations for the restriction endonuclease cleavage sites are as follows: Ba=BamHI; Bg=BgIII; H=HindIII; R=EcoRI; S=SphI; and X=XbaI. A one kilobase scale marker is also illustrated.

The radioactively labeled 2.4 kb cryIIIB gene was then used as a DNA probe under conditions that permitted the probe to bind specifically to those transformed host colonies that contained the 7.0 kb EcoRI-XbaI fragment of DNA from B.t. strain EG5144. Several E. coli colonies specifically hybridized to the 2.4 kb cryIIIB probe. One cryIIIB-hybridizing colony, designated E. coli strain EG7236, was studied further. E. coli strain EG7236 contained a recombinant plasmid, designated pEG271, which consisted of pUCI plus the inserted EcoRI-XbaI restriction fragment of DNA from B.t. strain EG5144 of approximately 7.0 kb. The cryIIIB probe specifically hybridized to the 7.0 kb DNA fragment insert in pEG271. A restriction map of pEG271 is shown in FIG. 5.

The 7.0 kb fragment of pEG271 contained HindIII fragments of 2.4 kb and 3.8 kb, and a BamHI-XbaI fragment of 4.0 kb that specifically hybridized with the cryIIIB probe. The 2.4 kb HindIII fragment was subcloned into the DNA sequencing vector M13mp8. The 4.0 kb BamHI-XbaI fragment was subcloned into the DNA sequencing vectors M13mp18 and M13mp19.

The nucleotide base sequence of a substantial part of each subcloned DNA fragment was determined using the standard Sanger dideoxy method. For each subcloned fragment, both DNA strands were sequenced by using sequence-specific 17-mer olignucleotide primers to initiate the DNA sequencing reactions. Sequencing revealed that the 7.0 kb fragment contained an open reading frame and, in particular, a new cryIII-type gene. This new gene, designated cryIIIC(b](SEQ ID NO:1), is significantly different from the cryIIIA gene. As indicated below, the cryIIIC(b) gene is also clearly distinct from the cryIIIB gene.

The DNA sequence of the cryIIIC(b) gene (SEQ ID NO:1) and the deduced amino acid sequence of the CryIIIC(b) protein (SEQ ID NO:2) encoded by the cryIIIC(b) gene are shown in FIG. 1. The protein coding portion of the cryIIIC(b) gene (SEQ ID NO:1) is defined by the nucleotides starting at position 144 and ending at position 2099. The probable ribosome binding site is indicated as "RBS" in FIG. 1A. The size of the CryIIIC(b) protein (SEQ ID NO:2) encoded by the cryIIIC(b) gene, as deduced from the open reading frame of the cryIIIC(b) gene (SEQ ID NO:1), is 74,265 Da (652 amino acids). It should be noted that the apparent size of the CryIIIC(b) protein, as determined from SDS-PAGE, is approximately 70 kDa. Therefore, the CryIIIC(b) protein (SEQ ID NO:2) will be referred to in this specification as being approximately 70 kDa in size.

The size of the prior art CryIIIA protein has previously been deduced to be 73,116 Da (644 amino acids). The size of the CryIIIB protein has previously been determined to be 74,237 Da (651 amino acids).

DNA sequencing revealed the presence of a HindIII restriction site within the cryIIIC(b) gene and a SspI restriction site downstream of the cryIIIC(b) gene (See FIGS. 1B and 1C respectively). Knowledge of the locations of these restriction sites permitted the precise determination of the location and orientation of the cryIIIC(b) gene within the 7.0 kb fragment as indicated by the arrow in FIG. 5.

The computer program of Korn and Queen (L. J. Korn and C. Queen, "Analysis of Biological Sequences on Small Computers," DNA, 3, pp. 421-436 (1984)) was used to compare the sequences of the cryIIIC(b) gene (SEQ ID NO:1) to the cryIIIB and cryIIIA genes and to compare the deduced amino acid sequences of their respective CryIIIC(b), CryIIIB and CryIIIA proteins.

The nucleotide base sequence of the cryIIIC(b) gene (SEQ ID NO:1) was 96% positionally identical with the nucleotide base sequence of the cryIIIB gene and only 76% positionally identical with the nucleotide base sequence of the cryIIIA gene. Thus, although the cryIIIC(b) gene (SEQ ID NO:1) is related to the cryIIIB and cryIIIA genes, it is clear that the cryIIIC(b) gene is distinct from the cryIIIB gene and substantially different from the cryIIIA gene.

The deduced amino acid sequence of the CryIIIC(b) protein (SEQ ID NO:2) was found to be 95% positionally identical to the deduced amino acid sequence of the CryIIIB protein, but only 68% positionally identical to the deduced amino acid sequence of the CryIIIA protein. These differences, together with the differences in insecticidal activity as set forth below, clearly show that the CryIIIC(b) protein encoded by the cryIIIC(b) gene (SEQ ID NO:1) is a different protein from the CryIIIB protein or the CryIIIA protein.

Moreover, while not wishing to be bound by any theory, based on a comparison of the amino acid sequences of the CryIIIC(b) protein (SEQ ID NO:2) with other CryIII-type proteins known to the inventors, it is believed that the following amino acid residues may be of significance for the enhanced corn rootworm toxicity of the CryIIIC(b) protein, where the numbers following the accepted abbreviations for the amino acids indicate the position of the amino acid in the sequence illustrated in FIG. 1 and identified in SEQ ID NO:2: His9, His231, Gln339, Ser352, Asn446, His449, Val450, Gly451, Ile600 and Thr624. These amino acid residues were selected as being of probable significance for the corn rootworm toxicity of the CryIIIC(b) protein (SEQ ID NO:2) because, after studying the amino acid sequences of several other CryIII proteins, the amino acids at the indicated positions fairly consistently showed different amino acids than those indicated for the CryIIIC(b) protein.

Based on the same studies, it is also believed that site directed mutagenesis of the cryIIIC(b) gene (SEQ ID NO:1) may result in improved or enhanced corn rootworm toxicity for the resultant protein where one or more of the following amino acid modifications are effected: Pro21 to Gly; Asp97 to Asn; Val289 to Ile; Ser352 to Phe 417Ile to Val; Phe419 to Leu; Gly451 to Ser; Ile590 to Leu; Ile600 to Lys; Thr624 to Lys.

As is well understood in the art, other changes in the cryIIIC(b) gene (SEQ ID NO:1) may be made, via site directed mutagenesis or gene truncation or the like, that could yield a toxic protein which possesses essentially similar insecticidal activity (to corn rootworm and other coleopteran insects) as that exhibited by the CryIIIC(b) protein (SEQ ID NO:2). Modifications to the cryIIIC(b) gene (SEQ ID NO:1) and CryIIIC(b) protein (SEQ ID NO:2) such as described above are intended to be within the scope of the claimed invention.

EXAMPLE 7

Expression of the Cloned cryIII(b) Gene

Studies were conducted to determine the production of the CryIIIC(b) protein (SEQ ID NO:2) by the cryIIIC(b) gene (SEQ ID NO:1).

Table 2 summarizes the relevant characteristics of the B.t. and *E. coli* strains and plasmids used during these procedures. A plus (+) indicates the presence of the designated element, activity or function and a minus (−) indicates the absence of the same. The designations s and r indicate sensitivity and resistance, respectively, to the antibiotic with which each is used. The abbreviations used in the Table have the following meanings: Amp (ampicillin); Cm (chloramphenicol); Cry (crystalliferous); Tc (tetracycline).

TABLE 2

| Strains | Strains and Plasmids<br>Relevant characteristics |
|---|---|
| *B. thuringiensis* | |
| HD73-26 | $Cry^-$, $Cm^s$ |
| EG7237 | HD73-26 harboring pEG272 (cryIIIC(b)$^+$) |
| EG5144 | cryIIIC(b)$^+$ |
| *E. coli* | |
| DH5α | $Cry^-$, $Amp^s$ |
| GM2163 | $Cry^-$, $Amp^s$ |
| EG7236 | DH5α harboring pEG271 (cryIIIC(b)$^+$) |
| Plasmids | |
| pUC18 | $Amp^r$, $Cry^-$, *E. coli* vector |
| pNN101 | $Cm^r$, $Tc^r$, $Cry^-$, Bacillus vector |
| pEG271 | $Amp^r$, cryIIIC(b)$^+$ *E. coli* recombinant plasmid consisting of the 7.0 kb EcoRI-XbaI cryIIIC(b)$^+$ fragment of B.t. strain EG5144 ligated into the EcoRI-XbaI sites of pUC18 |
| pEG272 | $Tc^r$, $Cm^r$, cryIIIC(b)$^+$ Bacillus-*E. coli* recombinant plasmid consisting of the Bacillus vector pNN101 ligated into the SphI site of pEG271. |

*E. coli* cells harboring plasmid peG271 described in Example 6 were analyzed and found not to produce detectable amounts of the 70 kDa CryIIIC(b) crystal protein.

Experience has shown that cloned B.t. crystal genes are poorly expressed in *E. coli* and highly expressed in B.t. from their respective native promoter sequences. Recombinant plasmid pEG271, constructed as set forth in Example 6 and shown in FIG. 5, will replicate in E. coli, but will not replicate in B.t. To achieve a high level of expression of the cloned cryIIIC(b) gene, the Bacillus vector pNN101 ($Tc^rCm^rCry^-$) that is capable of replicating in B.t. was ligated into the SphI site of pEG271. The resultant plasmid was designated pEG272. Details of the construction of plasmid pEG272 and its subsequent use to transform B.t. are described below.

The isolated plasmid pEG271 DNA was digested with SphI and was then mixed with the Bacillus vector pNN101 that had also been digested with SphI. T4 DNA ligase and ATP were added to the mixture to allow pEG271 to ligate into the SphI site of the pNN101 vector.

After ligation, the DNA mixture was added to a suspension of *E. coli* strain DH5α cells that had been treated with calcium chloride to permit the cells to take up plasmid DNA. After exposure to the recombinant plasmids, the *E. coli* host cells were spread on an agar medium containing tetracycline. Only cells that had taken up a plasmid consisting of pEG271 ligated into the SphI site of pNN101 would grow on the tetracycline agar medium whereas cells that had not absorbed the plasmid would not grow.

Figure 6:
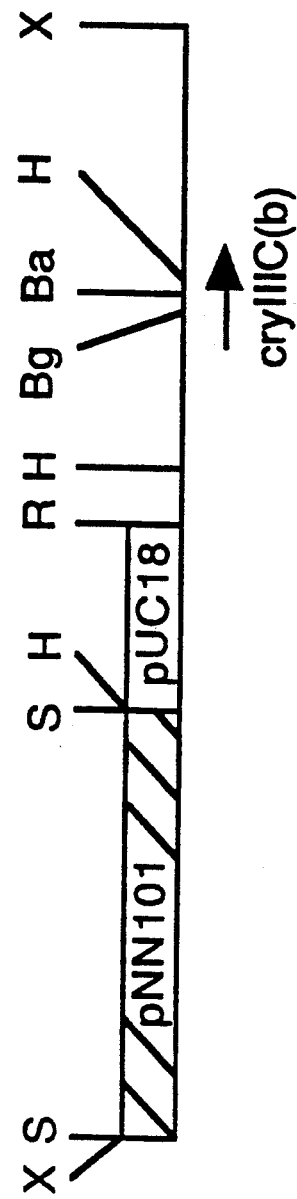
FIG. 6, aligned with and based on the same scale as FIG. 5, shows a restriction map of plasmid pEG272. The location and orientation of the cryIIIC(b) gene (SEQ ID NO:1) is indicated by the arrow shown in FIG. 5. Plasmid pEG272 is derived from plasmid pEG271 (FIG. 5) and contains the Bacillus plasmid pNN101 (Cm$^r$ Tc$^r$), indicated by the segment marked pNN101 and is incorporated into the SphI site of pEG271; this plasmid is functional in B.t. Abbreviations are the same as those for FIG. 5.

Plasmid was isolated from one tetracycline resistant colony, digested with SphI, and electrophoresed through an agarose gel. The plasmid consisted of two SphI DNA fragments of 5.8 kb and 9 kb corresponding to plasmids pNN101 and pEG271, respectively. This plasmid was designated pEG272. A restriction map of pEG272 is shown in FIG. 6. Plasmid pEG272 was then used to transform cells of *E. coli* strain GM2163 made competent by the calcium chloride procedure described earlier in Example 6. *E. coli* strain GM2163 is a crystal negative (Cry$^-$) and ampicillin sensitive (Amp$^s$) strain, constructed by the procedures of M. G. Marinus et al. in Mol.Gen.Genet., 192, pp.288-289 (1983).

Plasmid pEG272 was then isolated from the transformed *E. coli* strain GM2163, using the procedures described above. The isolated plasmid pEG272 was next transformed by electroporation into B.t. strain HD73-26. Cells of B.t. strain HD73-26 are crystal-negative (Cry$^-$) and chloramphenicol sensitive (Cm$^s$). Using a BioRad Gene Pulser ™ apparatus to carry out the electroporation, cells of B.t. strain HD73-26 in suspension were induced to take up pEG272 which was also added to the mixture.

After electroporation, the transformed B.t. cells were spread onto an agar medium containing 5 μg chloramphenicol and were incubated about 16–18 hours at 30° C. Cells that had taken up plasmid pEG272 would grow into colonies on the chloramphenicol agar medium whereas cells that had not absorbed the plasmid would not grow. One $Cm^r$ colony, designated B.t. strain EG7237, contained a plasmid whose restriction pattern appeared identical to that of pEG272.

Cells of B.t. strain EG7237 were grown in a sporulation medium containing chloramphenicol (3 μg/ml) at 22°–25° C. until sporulation and cell lysis had occurred (4–5 days). Microscopic examination revealed that the sporulated culture of B.t. strain EG7237 contained spores and small free floating irregularly shaped crystals. These crystals resembled the small, irregularly-shaped crystals observed with a sporulated culture of B.t. strain EG5144 that had been prepared in a similar manner.

Spores, crystals and cell debris from the sporulated fermentation culture of B.t. strain EG7237 were harvested by centrifugation. The centrifuge pellet was washed once with 1N aqueous NaCl and twice with TETX (10 mM Tris·HCl pH 7.5, 1 mM EDTA, 0.005% (w/v) Triton® X-100), and the pellet suspended in TETX at a concentration of 50 mg pellet/ml TETX.

The crystals in the centrifuge pellet suspension were solubilized by heating a portion of the centrifuge suspension (containing 250 μg pellet solids) in solubilization buffer (0.14 M Tris pH 6.8, 2% (w/v) SDS, 5% (v/v) 2-mercaptoethanol, 10% (v/v) glycerol and 0.1% (w/v) bromophenol blue) at 100° C. for 5 minutes. After crystal solubilization had occurred, the mixture was applied to an SDS-polyacryamide gel and the solubilized proteins in the mixture were size fractionated by electrophoresis. After size fractionization, the proteins were visualized by staining with Coomassie dye. A photograph of the Coomassie stained gel is shown in FIG. 7.

Lane 3 of the gel in FIG. 7 shows that B.t. strain EG7237 produced a major protein of approximately 70 kDa and a minor protein of approximately 30 kDa. These proteins appeared to be identical in size with the major approximately 70 kDa protein and the minor approximately 30 kDa protein produced by B.t. strain EG5144, which are shown in the lane 1 of FIG. 7 and which were prepared in a manner identical to B.t. strain EG7237. This result indicates that the 7.0 kb fragment of pEG272 contains two crystal protein genes: one for the approximately 70 kDa protein and one for the approximately 30 kDa protein.

The gene encoding the approximately 70 kDa protein is the cryIIIC(b) gene, and its encoded protein is the insecticidal CryIIIC(b) protein. The DNA sequence for the cryIIIC(b) gene (SEQ ID NO:1) and the amino acid sequence for its corresponding deduced protein (SEQ ID NO:2) are shown in FIG. 1.

B.t. strain EG7237 produced approximately three times more 70 kDa protein, on a weight basis, than did B.t. strain EG5144, as is evident from the protein bands in FIG. 7. Production of the minor 30 kDa protein in recombinant B.t. strain EG7237 was also increased, as compared with B.t. strain EG5144.

The following Examples 8–11 describe the manner in which the insecticidal activities of B.t. strain EG5144, B.t. strain EG7237, and the CryIIIC(b) protein made by these strains were determined.

EXAMPLE 8

Insecticidal Activity of B.t. Strain EG7237 and its CrYIIIC(b) Protein Against Southern Corn Rootworm and Colorado Potato Beetle The insecticidal activity of recombinant B.t. strain EG7237, which contains the cryIIIC(b) gene (SEQ ID NO:1) that produces the CryIIIC(b) toxin protein (SEQ ID NO:2), was determined against southern corn rootworm (*Diabrotica undecimpunctata howardi*) and Colorado potato beetle (*Leptinotarsa decemlineata*).

For comparison, two other recombinat B.t. strains containing cryIII-type toxin genes in a B.t. strain HD73-26 background were also included in the bioassay study. These were recombinant B.t. strain EG7235, which contains the cryIIIA gene that produces the CryIIIA toxin protein, and recombinant B.t. strain EG7225, which contains the cryIIIB gene that produces the CryIIIB toxin protein.

The three B.t. strains were grown in liquid sporulation media at 30° C. until sporulation and cell lysis had occurred. The fermentation broth was concentrated by microfiltration. The concentrated fermentation broth was then freeze dried to prepare a B.t. powder suitable for insect bioassay. The amount of CryIII-type toxin protein in each of the B.t. powders was quantified using standard SDS-PAGE techniques.

First instar southern corn rootwom larvae were bioassayed via surface contamination of an artificial diet similar to Marrone et al., *J.Econ.Entomol.*, 78, pp.290–293 (1985), but without formalin. Each bioassay consisted of eight serial aqueous dilutions with aliquots applied to the surface of the diet in a bioassay tray. Each 2 ml well of the bioassay tray contained 1 ml diet having a surface area of 175 $mm^2$. After the diluent (an aqueous 0.005% Triton® X-100 solution) had evaporated, the insect larvae were placed on the diet and incubated at 28° C. Thirty-two larvae were tested per dose. Mortality was scored after 7 days. A control, consisting of diluent only, was also included in the bioassay study.

First instar Colorado potato beetle larvae were tested using similar techniques, except for the substitution in the artificial diet of BioServe's No. 9830 insect diet with potato flakes added. Thirty-two larvae were tested per dose, and mortality was scored at three days instead of seven days.

The results of the bioassay study are shown below in Table 3, where insecticidal activity is reported as PLC$_{50}$ values, the concentration of CryIII-type protein required to kill 50% of the insects tested. Four replications per dose were used in the bioassay studies for both insects tested. Data from each of the replicated bioassays were pooled for probit analysis (R. J. Daum, *Bull. Entomol.Soc.Am.*, 16, pp.10-15 (1970)) with mortality corrected for control death, the control being the diluent only (W. S. Abbott, *J.Econ.Entomol.*, 18, pp.265-267 (1925)). Results are shown as the dose amount of CryIII-type protein (in ng CryIII protein per mm$^2$ of diet surface) resulting in PLC$_{50}$. Confidence intervals, at 95%, are given within parentheses below the PLC$_{50}$ values.

TABLE 3

| | | | Insecticidal Activity of Recombinant B.t. Strains EG7237, EG7235 and EG7225 | |
|---|---|---|---|---|
| B.t. Strain | CryIII Protein | CryIII Protein Concentration (%) | Southern Corn Rootworm PLC$_{50}$ (ng CryIII protein/mm$^2$) | Colorado Potato Beetle PLC$_{50}$ (ng CryIII protein/mm$^2$) |
| B.t. EG7237 | CryIIIC(b) | 7.2 | 1548 (1243-1992) | 6.92 (5.15-9.10) |
| B.t. EG7235 | CryIIIA | 28.4 | 6% control at 4570 | 0.34 (0.30-0.39) |
| B.t. EG7225 | CryIIIB | 9.4 | 20% control at 4570 | 1.26 (1.07-1.46) |

The results of this bioassay study demonstrate that B.t. strain EG7237 which produces the CryIIIC(b) toxin protein (SEQ ID NO:2) is insecticidal to southern corn rootworm. In contrast, the CryIIIA and CryIIIB toxin proteins of B.t. strains EG7235 and EG7225, respectively, appear to have no measurable activity against this insect at the highest dose level tested.

All three of the B.t. strains exhibit insecticidal activity against Colorado potato beetle larvae, with the CryIIIA toxin protein of B.t. strain EG7235 being significantly more potent than the CryIIIC(b) toxin protein (SEQ ID NO:2) of B.t. strain EG7237 and with the CryIIIB toxin protein of B.t. strain EG7225 having insecticidal activity falling between that shown for CryIIIA and CryIIIC(b).

These results suggest that the insecticidal activity of specific CryIII-type toxin proteins varies for different insect genera within the order Coleoptera.

EXAMPLE 9

Insecticidal Activity of B.t. Strain EG7237 and its CryIIIC(b) Protein Against Mexican Bean Beetle The insecticidal activity of recombinant B.t. strain EG7237, evaluated in Example 8, was also determined against Mexican bean beetle (*Epilachna varivestis*). As in Example 8, recombinant B.t. strains EG7235 and EG7225 were included for comparison, and all B.t. powders were prepared as in Example 8.

First instar Mexican bean beetle larvae were bioassayed by a leaf dip procedure, since a suitable artificial diet is not available for this insect. Soybean leaves were dipped into known treatment concentrations of the B.t. powder suspended in an aqueous 0.1% Triton ®X-100 solution. After excess material had dripped off, the leaves were allowed to dry. Leaves dipped in 0.1% Triton ® X-100 served as untreated controls. Twenty insect larvae were confined to a petri dish with treated leaves, incubated at 25° C., and allowed to feed for three days, at which time mortality was scored.

The results of the bioassay study are shown below in Table 4, where insecticidal activity is reported as PLC50 values, the concentration of CryIII-type protein required to kill 50% of the insects tested. The data were handled as described in Example 8, for Table 3. Results are shown as the dose amount of CryIII-type protein (in mg CryIII protein/ml solution used in the leaf dip) resulting in PLC$_{50}$. Confidence intervals, at 95%, are given within parentheses following the PLC$_{50}$ values.

TABLE 4

| Insecticidal Activity of B.t. Strains EG7237, EG7235 and E7225 Against Mexican Bean Beetle | | | |
|---|---|---|---|
| B.t. Strain | CryIII Protein | No. of Replications | PLC$_{50}$ (mg CryIIIprotein/ml) |
| B.t. EG7237 | CryIIIC(b) | 4 | 4.2 (2.5-6.5) |
| B.t. EG7235 | CryIIIA | 4 | 16% control at 60 |
| B.t. EG7225 | CryIIIB | 4 | 51.8 (31-209) |

The results of this bioassay study demonstrate that B.t. strain EG7237 which produces the CryIIIC(b) toxin protein (SEQ ID NO:2) is significantly more insecticidal to Mexican bean beetle than the CryIIIB-producing B.t. strain EG7225. B.t. strain EG7235 which produces CryIIIA toxin protein exhibited no measurable insecticidal activity at the highest dose tested.

These results are further evidence that the insecticidal activity of specific CryIII-type toxin proteins varies widely for insect genera within the order Coleoptera.

EXAMPLE 10

Insecticidal Activity of B.t. strain EG5144 Against Southern Corn Rootworm

The insecticidal activity of B.t. strain EG5144 was evaluated against Southern corn rootworm (*Diabrotica undecimpunctata howardi*). For comparison, B.t. strain EG4961 which produces the CryIIIC(a) toxin protein was included in the bioassay study.

The bioassay procedure for southern corn rootworm in this Example determined PLC50 values, the concentration of CryIII-type protein required to kill 50% of the insects tested. The procedure was similar to the artificial diet bioassay carried out in the previous Example, using thirty-two first instar southern corn rootworm larvae per dose. Data from each of the replicated bioassays were pooled for probit analysis (R. J. Daum, Bull.Entomol.Soc.Am., 16, pp.10-15 (1970)) with mortality corrected for control death, the control being the diluent only (W. S. Abbott, *J.Econ.Entomol.*, 18, pp.265-267 (1925)). Results are reported for two separate tests as the dose amount of CryIII-type protein (ng CryIII protein per mm² of diet surface) resulting in PLC$_{50}$. Confidence intervals, at 95%, are given within parentheses following the PLC50 values. In Test 1 four replications per dose were used, and in Test 2, carried out at a later date, two replications were used.

The B.t. strains used in this Example were prepared as described for the B.t. strains in Example 8, except that the fermentation broth was concentrated by centrifugation.

The results of this bioassay study with southern corn rootworm are shown below in Table 5.

TABLE 5

Insecticidal Activity of B.t. Strains EG5144 and EG4961 Aainst Southern Corn RootWorm

| B.t. Strain | CryIII Protein | | CryIII Protein Concentration (%) | PLC$_{50}$ (ng CryIII porotein/mm²) |
| --- | --- | --- | --- | --- |
| B.t. EG5144 | CryIIIC(b) | Test 1: | 4.0 | 944 (690–1412) |
|  |  | Test 2: | 6.4 | 1145 (773–2185) |
| B.t. EG4961 | CryIIIC(a) | Test 1: | 11.6 | 102 (86–119) |
|  |  | Test 2: | 11.6 | 165 (121–220) |

This bioassay study demonstrates that both B.t. strain EG5144 and B.t. strain EG4961, which produce CryIIIC-type proteins, provide quantifiable insecticidal activity against southern corn rootworm.

EXAMPLE 11

Insecticidal Activity of B.t. Strain EG5144 Against Japanese Beetle Larvae

The insecticidal activity of B.t. strain EG5144 was evaluated against Japanese beetle larvae, also known as white grubs (*Popillia japonica*). For comparison, B.t. strain EG4961 which produces the CryIIIC(a) toxin protein was included in the bioassay study, as were B.t. strain EG2158 which produces the CryIIIA toxin protein and B.t. strain EG2838 which produces the CryIIIB toxin protein.

The bioassay procedure in this Example was a screening assay, at a single dose of CryIII-type protein in a diet incorporation assay (1 mg CryIII-type protein per ml diet). B.t. powder to be tested, suspended in a diluent (an aqueous 0.005% Triton ® X-100 solution) was incorporated into 100 ml of hot (50°–60° C.), liquid artificial diet (based on the insect diet described by Ladd, Jr. in J.Econ.Entomol., 79, pp.668–671 (1986)). The mixture was allowed to solidify in petri dishes, and one 19 mm diameter plug of this material then placed in each well of a plastic ice cube tray. One grub was introduced per well of the trays, the wells were covered with moist germination paper overlaid with aluminum foil, and the trays were held at 25° C. for seven days before mortality was scored. The insects tested were third instar Japanese beetle grubs. Two replications of sixteen insects each were carried out in this study.

The results of this screening bioassay study are shown below in Table 6, where insecticidal activity is reported as percentage insect mortality, with the mortality being corrected for control death, the control being diluent only incorporated into the diet plug. Results were obtained at a single dose rate of CryIII-type protein: 1 mg CryIII-type protein per ml of diet; percentage CryIII-type protein present in the respective B.t. powders is also shown in Table 6.

TABLE 6

Insecticidal Activity of B.t. Strains EG5144, EG4961, EG2158 and EG2838 Against Japanese Beetle Grubs

| B.t. Strain | CryIII Protein | CryIII-type Protein in B.t. Powder (wt. %) | CryIII-type Protein Dose (mg CryIII-type protein/ml diet) | Insect Mortality (%) |
| --- | --- | --- | --- | --- |
| B.t. EG5144 | CryIIIC(b) | 5.4 | 1 | 62.5 |
| B.t. EG4961 | CryIIIC(a) | 18.0 | 1 | 9 |
| B.t. EG2158 | CryIIIA | 14.0 | 1 | 44 |
| B.t. EG2838 | CryIIIB | 7.2 | 1 | 48 |

The insecticidal performance against Japanese beetle grubs of B.t. strain EG5144 with its CryIIIC(b) toxin protein (SEQ ID NO:2) is clearly superior to that of B.t. strain EG4961 with its CryIIIC(a) protein.

With respect to B.t. strains EG2158 and B.t. strain EG2838, B.t. strain EG5144 exhibited superior insecticidal performance against Japanese beetle grubs.

B.t. strain EG5145, whose characteristics are similar to those of B.t. strain EG5144, has been found to exhibit insecticidal activity against Japanese beetle grubs equivalent to that of B.t. strain EG5144, although the bioassay data are not presented in this Example 11.

Microorganism Deposits

To assure the availability of materials to those interested members of the public upon issuance of a patent on the present application, deposits of the following microorganisms were made prior to the filing of present application with the ARS Patent Collection, Agricultural Research Culture Collection, Northern Regional Research Laboratory (NRRL), 1815 North University Street, Peoria, Ill. 61604, as indicated in the following Table 7:

TABLE 7

| Bacterial Strain | NRRL Accession No. | Date of Deposit |
| --- | --- | --- |
| B.t. EG2158 | B-18213 | April 29, 1987 |
| B.t. HD73-26 | B-18508 | June 12, 1989 |
| B.t. EG2838 | B-18603 | February 8, 1990 |
| B.t. EG5144 | B-18655 | May 22, 1990 |
| B.t. EG7237 | B-18736 | October 17, 1990 |
| E. coli EG7236 | B-18662 | June 6, 1990 |
| B.t. EG5145 | B-18920 | November 21, 1991 |

These microorganism deposits were made under the provisions of the "Budapest Treaty on the International Recognition of the Deposit of Microorganisms for the Purposes of Patent Procedure". All restrictions on the availability to the public of these deposited microorganisms will be irrevocably removed upon issuance of a United States patent based on this application.

The present invention may be embodied in other specific forms without departing from the spirit or essential attributes thereof and, accordingly, reference should be made to the appended claims, rather than to the foregoing specification as indicating the scope of the invention.

We claim:

1. A purified and isolated cryIIIC(b) gene having a nucleotide base sequence coding for the amino acid sequence illustrated in FIG. 1 (SEQ ID NO:2).

2. A purified and isolated cryIIIC(b) gene according to claim 1 wherein the gene has a coding region extending from nucleotide bases 144 to 2099 in the nucleotide base sequence illustrated in FIG. 1 (SEQ ID NO:1).

3. A recombinant plasmid containing the gene of claim 1 or 2.

4. A biologically pure culture of a bacterium transformed with the recombinant plasmid of claim 3.

5. The bacterium of claim 4 wherein the bacterium is *Bacillus thuringiensis*.

6. The *Bacillus thuringiensis* bacterium of claim 5 deposited with the NRRL having accession number NRRL B-18736.

7. The cryIIIC(b) gene of claim 2 wherein the gene or a portion thereof is labelled for use as a hybridization probe.

8. A biologically pure culture of a *Bacillus thuringiensis* bacterium deposited with the NRRL having accession number NRRL B-18655.

9. A biologically pure culture of a *Bacillus thuringiensis* bacterium deposited with the NRRL having accession number NRRL B-18920.

* * * * *